US011763696B2

(12) United States Patent
Banerji

(10) Patent No.: US 11,763,696 B2
(45) Date of Patent: Sep. 19, 2023

(54) SYSTEMS AND METHODS FOR FACILITATING MIND-BODY-EMOTION STATE SELF-ADJUSTMENT AND FUNCTIONAL SKILLS DEVELOPMENT BY WAY OF BIOFEEDBACK AND ENVIRONMENTAL MONITORING

(71) Applicant: SYNPHNE PTE LTD., Singapore (SG)

(72) Inventor: Subhasis Banerji, Singapore (SG)

(73) Assignee: SYNPHNE PTE LTD, Singapore (SG)

( * ) Notice: Subject to any disclaimer, the term of this patent is extended or adjusted under 35 U.S.C. 154(b) by 449 days.

(21) Appl. No.: 15/768,556

(22) PCT Filed: Oct. 14, 2016

(86) PCT No.: PCT/SG2016/050507
§ 371 (c)(1),
(2) Date: Apr. 15, 2018

(87) PCT Pub. No.: WO2017/065694
PCT Pub. Date: Apr. 20, 2017

(65) Prior Publication Data
US 2018/0301054 A1  Oct. 18, 2018

Related U.S. Application Data

(60) Provisional application No. 62/241,715, filed on Oct. 14, 2015.

(51) Int. Cl.
*G09B 19/00* (2006.01)
*A61B 5/00* (2006.01)
(Continued)

(52) U.S. Cl.
CPC ............ *G09B 19/00* (2013.01); *A61B 5/0022* (2013.01); *A61B 5/0024* (2013.01);
(Continued)

(58) Field of Classification Search
CPC ............... G09B 19/00; A61B 2505/09; A61B 2560/0252; A61B 2560/0257;
(Continued)

(56) References Cited

U.S. PATENT DOCUMENTS

2006/0100546 A1 *  5/2006  Silk .................... A61B 5/1038
600/592
2008/0214903 A1    9/2008  Orbach
(Continued)

FOREIGN PATENT DOCUMENTS

WO    2015044851 A2    4/2015

*Primary Examiner* — Eddy Saint-Vil
(74) *Attorney, Agent, or Firm* — HORIZON IP PTE LTD

(57) ABSTRACT

A system for aiding a subject development of physical, mental, and/or emotional skills, subject awareness of their mind state, body state, and/or emotional state, and providing subject biofeedback includes subject-internal signal sensing devices wearable by the subject for sensing signals generated internal to the subject's body; subject-external signal sensing devices for sensing signals generated external to the subject's body; a local computing unit configured for authenticated wireless communication with the subject-internal and subject-external signal sensing devices, and presenting particular types of mind state, body state, and emotional state information to the subject, for instance, in the form of biofeedback (e.g., mind-body state biofeedback, and/or mind-body-emotion state biofeedback); and a cellular network communication unit configured for communicating data corresponding to sensed subject-internal signals and sensed subject-external signals to at least one server by way of at least one cellular network.

21 Claims, 14 Drawing Sheets

(51) Int. Cl.
*A61B 5/16* (2006.01)
*A61B 5/11* (2006.01)
*A61B 5/0205* (2006.01)
*A61B 5/24* (2021.01)
*A61B 5/291* (2021.01)
*A61B 5/369* (2021.01)
*A61B 5/374* (2021.01)
*A61B 5/389* (2021.01)
*A61B 5/024* (2006.01)
*A61B 5/08* (2006.01)

(52) U.S. Cl.
CPC .......... *A61B 5/0205* (2013.01); *A61B 5/1118* (2013.01); *A61B 5/165* (2013.01); *A61B 5/486* (2013.01); *A61B 5/4854* (2013.01); *A61B 5/02405* (2013.01); *A61B 5/082* (2013.01); *A61B 5/1122* (2013.01); *A61B 5/168* (2013.01); *A61B 5/24* (2021.01); *A61B 5/291* (2021.01); *A61B 5/369* (2021.01); *A61B 5/374* (2021.01); *A61B 5/389* (2021.01); *A61B 2505/09* (2013.01); *A61B 2560/0252* (2013.01); *A61B 2560/0257* (2013.01); *A61B 2562/0219* (2013.01)

(58) Field of Classification Search
CPC .......... A61B 2562/0219; A61B 5/0022; A61B 5/0024; A61B 5/0205; A61B 5/02405; A61B 5/04001; A61B 5/0476; A61B 5/0478; A61B 5/048; A61B 5/0488; A61B 5/082; A61B 5/1118; A61B 5/1122; A61B 5/165; A61B 5/168; A61B 5/4854; A61B 5/486

See application file for complete search history.

(56) References Cited

U.S. PATENT DOCUMENTS

| | | |
|---|---|---|
| 2009/0221928 A1 | 9/2009 | Einav et al. |
| 2011/0054272 A1* | 3/2011 | Derchak ............ A63B 24/0003 600/301 |
| 2011/0061647 A1* | 3/2011 | Stahmann .......... A61B 5/02405 128/202.16 |
| 2011/0213278 A1* | 9/2011 | Horak ................. A61B 5/4082 600/595 |
| 2012/0310069 A1 | 12/2012 | Clare et al. |
| 2013/0089840 A1* | 4/2013 | Drane .................... G09B 19/00 434/219 |
| 2013/0190658 A1* | 7/2013 | Flaction ................ A61B 5/112 600/595 |
| 2014/0200432 A1 | 7/2014 | Banerji et al. |
| 2014/0371633 A1* | 12/2014 | Evin .................... A61B 5/1128 600/595 |
| 2015/0035680 A1* | 2/2015 | Li ........................ A61B 5/6833 340/584 |
| 2015/0179050 A1 | 6/2015 | Katingari et al. |
| 2015/0199010 A1 | 7/2015 | Coleman et al. |
| 2015/0241998 A1 | 8/2015 | VanBlon et al. |
| 2015/0305675 A1* | 10/2015 | Miller ................. A61B 5/6823 600/301 |
| 2016/0038037 A1* | 2/2016 | Kovacs ............... A61B 5/6887 600/301 |

* cited by examiner

FIG. 8A

Vewake State Table

| Guna (State) | Brain State (EEG) | Body State (EMG) | Emotion State (HRV) | Breath State (SpO2) |
|---|---|---|---|---|
| Sattwa (Relaxed & Full of Life) | High alpha, low delta, high overall power | Low baseline values in rest and relaxation | High Stability | High oxygenation |
| Rajas (Very Active but tendency to burn out) | High beta, high overall power, high thetha, low alpha | Rest baselines higher than relaxation, high MVC | Frequency Instability | Medium oxygenation |
| Tamas (Burned-out or sedentary & at risk for chronic diseases) | Low alpha, low beta, high delta, low overall power | Relaxation baselines chronically high, low MVC | Chronic Instability | Low oxygenation |
| Balance (Relaxed, Active, Full of Life) | High alpha, high overall power, high beta on need basis | Low baselines in rest and relaxation, high MVC on need basis, fast recovery | High Stability | High oxygenation |

FIG. 10

SYSTEMS AND METHODS FOR FACILITATING MIND-BODY-EMOTION STATE SELF-ADJUSTMENT AND FUNCTIONAL SKILLS DEVELOPMENT BY WAY OF BIOFEEDBACK AND ENVIRONMENTAL MONITORING

TECHNICAL FIELD

The present disclosure relates generally to biofeedback systems and methods, as well as subject skills development, rehabilitation, and wellness systems and methods, and systems and methods for capturing subject mind state, body state, and/or emotional state signals, and presenting such signals and/or information derived therefrom to the subject (e.g., by way of biofeedback) for purpose of aiding subject skills development, rehabilitation, and wellness.

BACKGROUND

Various types of systems, devices, and techniques directed to aiding or enhancing an impaired subject's development of neuromuscular function (e.g., fine motor control) and corresponding functional skills exist, and various types of systems, devices, and techniques directed to providing biofeedback to the subject during subject performance of tasks directed to aiding or enhancing neuromuscular function and corresponding functional skills. International Patent Publication No. WO/2012161657 describes particular types of systems, devices, and techniques in this regard, which provide for the generation of subject mind state signals and corresponding mind state measures and body state signals and corresponding body state measures, and the presentation of functional activity development sequences to a subject concurrent with the presentation of mind state and body state feedback to the subject.

A wide variety of factors can influence or affect (beneficially or adversely) subject neurofunctional state or performance, subject skills development, and the extent of subject receptivity to and the efficiency of subject auto-adaptivity or self-correction to biofeedback. Existing systems, devices, and techniques do not consider or operate based on certain factors that can significantly or dramatically aid subject functional skills development, subject wellness, and subject health. Additionally, existing systems, devices, and techniques can be cumbersome from the perspective of subjects and other individuals concerned with the subject's functional skills development, wellness, and health, such as caregivers, clinicians, researchers, and family members. Improved systems, devices, and techniques for facilitating or enhancing subject functional skills development and providing subject biofeedback are needed.

SUMMARY

Particular aspects of the present disclosure are directed to systems and methods in which signal sensing apparatuses or devices, including signal sensing apparatuses or devices worn by a subject, are configured for (a) capturing (i) signals generated internal to the subject's body (e.g., "subject-internal signals") including EEG, EMG, and possibly other physiologic/physiologic correlate signals (e.g., heart rate), as well as (ii) signals generated external to the subject's body (e.g., "subject-external signals") such as signals generated by devices worn by the subject and/or signals that exist in the subject's current external environment (e.g., temperature, relative humidity, ambient noise level, ambient lighting level, atmospheric pressure and/or altitude, ambient magnetic field intensity, ambient electromagnetic radiation levels or values in one or more portions of the electromagnetic frequency spectrum, and/or other signals); (b) transmitting such captured signals to a local computing unit; (c) analyzing such signals; (d) providing feedback to the subject, including biofeedback, based on such signals; and (e) providing information to other individuals, such as medical professionals, clinicians, researchers, caretakers, family members, or friends, based on such signals.

The local computing unit can be configured for analyzing signals/data received from the signal sensing apparatuses; generating measures of the subject's current mind state, body state, and possibly emotional state; presenting/displaying a visual representation of the subject's current mind state, body state, and possibly emotional state (e.g., relative to a target or synergistic mind state and body state, or a target or synergistic mind state, body state, and emotional state); selectively visually presenting/displaying representative skill/exercise sequences such as model movements in an adaptive manner based upon the subject's current and/or recent mind state, body state, and possibly emotional state, concurrent with presenting/displaying the visual representation of the subject's current mind state, body state, and possibly emotional state; generating subject session history information; and transmitting (1) signals/data received from the signal sensing apparatuses, (2) generated mind state measure, body state measure, and possibly emotional state measure histories, and (3) related user session history information to a set of servers for further analysis. The set of servers can provide a mind-body state and/or mind-body-emotion state education, maintenance/regulation, skills development, and social interaction/social media portal accessible to subjects, clinicians/therapists/researchers, and possibly other individuals (e.g., user family members or friends).

In accordance with an aspect of the present disclosure, a computerized process for aiding a human subject in the development of physical, mental, and/or emotional skills, aiding subject awareness of their mind state, body state, and/or emotional state, and providing subject biofeedback includes: sensing first subject-internal signals, the first subject-internal signals including physiologic signals generated internal to the subject's body including first neural activity signals, first muscle activity signals, and first heart rate variability signals; determining a baseline subject mind state, a baseline subject body state, and a baseline subject emotional state using the sensed first subject-internal signals; exposing the subject to a stressor including at least one of: (a) an emotional stressor including visual image or scene and/or audio information capable of producing a stressed subject emotional state, and (b) a physical stressor including a subject body condition or stimulus capable of producing a stressed subject physical state; sensing second subject-internal signals during and after exposing the subject to the stressor, the second subject-internal signals generated internal to the subject's body and including second neural activity signals, second muscle activity signals, and second heart rate variability signals; determining a stressed subject mind state, a stressed subject body state, and a stressed subject emotional state using the sensed second subject-internal signals; terminating exposure of the subject to the stressor; determining at least one of: (i-a) a mind state recovery time interval across which the stressed subject mind state returns to within a first target percentage of the baseline subject mind state; (ii-a) a body state recovery time interval across which the stressed subject emotional state returns to within a second target percentage of the baseline subject emotional state, and (iii-a) an emotional state recovery time interval across which the stressed subject body state returns to a third target percentage of the baseline subject body state; and determining or estimating a subject health state based on at least one of the mind state recovery time interval, the body state recovery time interval, and the emotional state recovery time interval.

Sensing the first and second neural activity signals can include sensing electroencephalography (EEG) signals, and sensing the first and second muscle activity signals includes sensing electromyography (EMG) signals.

When the subject has a physically impaired body part, determining the subject health state includes determining whether the at least one of the mind state recovery time interval, the body state recovery time interval, and the emotional state recovery time interval decreases over time following multiple subject physical skill development sessions, wherein each subject physical skill development session includes presenting functional skill development activities to the subject simultaneous with presenting current mind state biofeedback and current body state feedback to the subject, and wherein presenting the functional skill development activities includes presenting visual information showing usage of an unimpaired body part corresponding to the physically impaired body part in a mirror image manner during subject viewing of the visual information.

The process can further include determining at least one of: (i-b) a mind state recovery profile including a mind state measure recovery pattern that the stressed subject mind state exhibits as it returns toward the baseline subject mind state, (ii-b) a body state recovery profile including a body state measure recovery pattern that the stressed subject body state exhibits as it returns toward the baseline subject body state, and (iii-b) an emotional state recovery profile including an emotional state measure recovery pattern that the stressed subject emotional state exhibits as it returns toward the baseline subject mind state, wherein determining or estimating the subject health state is further based on at least one of the mind state recovery profile, the body state recovery profile, and the emotional state recovery profile.

The process can additionally include: determining an extent of subject torso or trunk rotational asymmetry; and determining whether the extent of subject torso or trunk rotational asymmetry is greater than a target or threshold torso or trunk rotational asymmetry value. The target or threshold torso or trunk rotational asymmetry value can equal 9 mm+/−20%. Determining the subject health state can further include determining whether the extent of subject torso or trunk rotational asymmetry decreases over time to less than or equal to the target or threshold torso or trunk rotational asymmetry value following the multiple subject physical skill development sessions.

The process can also include: sensing levels of subject-external signals, the subject-external signals generated external to the subject's body and including an ambient temperature level, an ambient relative humidity level, and an ambient noise level; determining subject performance and/or subject outcome measures corresponding to each physical skill development session; correlating the levels of sensed subject-external signals with the subject performance and/or subject outcome measures; and determining whether subject performance and/or subject outcome measures across different physical skill development sessions was adversely affected by the level of one or more subject-external signals exceeding a target or threshold level or falling outside of a target or threshold range. Determining levels of subject-external signals can include determining at least one of an ambient light level, an ambient atmospheric pressure or altitude level, an ambient magnetic field intensity level, and an ambient electromagnetic signal level within at least one electromagnetic signal frequency band.

The process can further include automatically transferring by way of cellular network communication the determined subject performance measures and/or subject outcome measures to a set of servers, without subject initiation, management, and/or acknowledgment. Determining subject outcome measures can include: capturing image data and/or audio data representing a current subject outcome resulting from subject performance or attempted performance of a functional development activity sequence; and comparing the received image data and/or audio data with target image data and/or audio data, respectively, to determine an extent to which the current subject outcome matches a target outcome for the functional development activity sequence.

In accordance with an aspect of the present disclosure, a system for aiding a subject in the development of physical, mental, and/or emotional skills, aiding subject awareness of their mind state, body state, and/or emotional state, and providing subject biofeedback includes: (a) a set of subject-internal signal sensing devices wearable by the subject and configured for sensing signals generated internal to the subject's body, the set of subject-internal signal sensing devices including: a head mountable sensing apparatus configured for sensing subject electroencephalography (EEG) signals; and at least one of: a forearm mountable sensing apparatus configured for sensing subject electromyography (EMG) signals generated by particular subject forearm and hand muscles, a neck mountable sensing apparatus configured for sensing EMG signals generated by particular subject neck muscles, a chest mountable sensing apparatus configured for sensing subject EMG signals generated by particular subject upper torso muscles, a waist/hip mountable apparatus configured for sensing EMG signals generated by particular subject abdominal, waist, hip, and/or gluteal region muscles; and an upper leg mountable sensing apparatus configured for sensing subject EMG signals generated by subject upper leg muscles; and a lower leg mountable apparatus configured for sensing EMG signals generated by particular subject lower leg muscles; (b) a set of subject-external signal sensing devices configured for sensing signals generated external to the subject's body, the set of subject-external sensing devices including: a set of accelerometers and/or gyroscopes carried by the set of subject-internal signal sensing devices; an ambient temperature sensor; an ambient humidity sensor; and an ambient noise sensor; (c) a local computing unit having a processing unit and a memory storing program instructions executable by the processing unit; (d) a display device configured for presenting biofeedback information to the subject simultaneous with presenting functional development activity sequences to the subject; and (e) a cellular network communication unit configured for communicating data corresponding to sensed subject-internal signals and sensed subject-external signals to at least one server by way of at least one cellular network. The set of subject-external signal sensing devices can also include at least one of an ambient lighting level sensor, an ambient atmospheric pressure or elevation level sensor, an ambient magnetic field intensity sensor, and an ambient electromagnetic signal level corresponding to at least one electromagnetic signal frequency band.

When subject has a physically impaired body part, the set of subject-internal signal sensing devices can be configured for sensing EMG signals generated by muscles within the impaired body part, and the presentation of the functional development activity sequences includes presenting visual information showing usage of an unimpaired body part corresponding to the physically impaired body part in a mirror image manner during subject viewing of the visual information.

The system can include a local wireless network communication and authentication unit coupled to the local computing unit, and wherein each subject-internal signal sensing device is configured for authenticated wireless network communication of sensed subject-internal signals to the local computing unit by way of the local wireless network communication and authentication unit.

The program instructions when executed by the processing unit can direct the system to: store sensed first subject-internal signals, the first subject-internal signals including physiologic signals generated internal to the subject's body including first neural activity signals, first muscle activity signals, and first heart rate variability signals; determine a baseline subject mind state, a baseline subject body state, and a baseline subject emotional state using the sensed first subject-internal signals; expose the subject to a stressor including at least one of: (a) an emotional stressor including visual image or scene and/or audio information capable of producing a stressed subject emotional state, and (b) a physical stressor including a subject body condition or stimulus capable of producing a stressed subject physical state; store sensed second subject-internal signals during and after exposing the subject to the stressor, the second subject-internal signals generated internal to the subject's body and including second neural activity signals, second muscle activity signals, and second heart rate variability signals; determine a stressed subject mind state, a stressed subject body state, and a stressed subject emotional state using the sensed second subject-internal signals; terminate exposure of the subject to the stressor; determine at least one of: (i-a) a mind state recovery time interval across which the stressed subject mind state returns to within a first target percentage of the baseline subject mind state; (ii-a) a body state recovery time interval across which the stressed subject emotional state returns to within a second target percentage of the baseline subject emotional state, and (iii-a) an emotional state recovery time interval across which the stressed subject body state returns to a third target percentage of the baseline subject body state; and determine or estimate a subject health state based on at least one of the mind state recovery time interval, the body state recovery time interval, and the emotional state recovery time interval.

Such program instructions when executed can further direct the system to: determine at least one of: (i-b) a mind state recovery profile including a mind state measure recovery pattern that the stressed subject mind state exhibits as it returns toward the baseline subject mind state, (ii-b) a body state recovery profile including a body state measure recovery pattern that the stressed subject body state exhibits as it returns toward the baseline subject body state, and (iii-b) an emotional state recovery profile including an emotional state measure recovery pattern that the stressed subject emotional state exhibits as it returns toward the baseline subject mind state; and determine or estimate the subject health state based on at least one of the mind state recovery profile, the body state recovery profile, and the emotional state recovery profile.

The program instructions when executed by the processing unit can also cause the system to: determine an extent of subject torso or trunk rotational asymmetry; determine whether the extent of subject torso or trunk rotational asymmetry is greater than a target or threshold torso or trunk rotational asymmetry value.

The system can additionally include: a set of servers including the at least one server; and a database with which the set of servers communicates, and which stores subject information including (a) sensed subject-internal signal histories and/or subject mind state measures, body state measures, and emotional state measures derived therefrom, sensed subject external signal histories including, (b) sensed subject-external signal histories, and (c) target subject outcome data representing target outcomes of subject performance or attempted performance of particular types of functional development activity sequences, wherein the set of servers includes at least one server processing unit and at least one server memory storing server program instructions which when executed by the at least one server processing unit cause the server to compare current subject outcome data associated with a specific functional development activity sequence and which was received from the local computing unit with corresponding target subject outcome data to determine an extent to which the current subject outcome data matches the target subject outcome data. The current subject outcome data can include at least one of image data, audio data, electronic drawing pad and/or electronic stylus data, captured keyboard input, accelerometer and/or gyroscope data generated by an apparatus or device with which the subject interacts, and pressure mat data.

The set of server program instructions when executed by the at least one server processing unit can also the set of servers to: correlate levels of sensed subject-external signals with subject performance measures and/or subject outcome measures corresponding to multiple physical skill development sessions including or involving subject performance or attempted performance of multiple functional activity development sequences over time; and determine whether subject performance and/or subject outcome measures across different physical skill development sessions was adversely affected by a level of one or more sensed subject-external signals exceeding a target or threshold level or falling outside of a target or threshold range.

BRIEF DESCRIPTION OF THE DRAWINGS

FIGS. 8A-8C are representative visual interfaces that a system in accordance with an embodiment of the present disclosure can provide to clinicians/therapists/researchers and possibly the subject in order to facilitate or enable measurement or generation of subject mind-body and/or mind-body-emotion related bio-markers, and visualization of results corresponding thereto.

FIG. 10 illustrates representative categorical types of composite mind-body-emotion state information that can be defined, calculated, and presented in accordance with an embodiment of the present disclosure.

DETAILED DESCRIPTION

Figure 1:
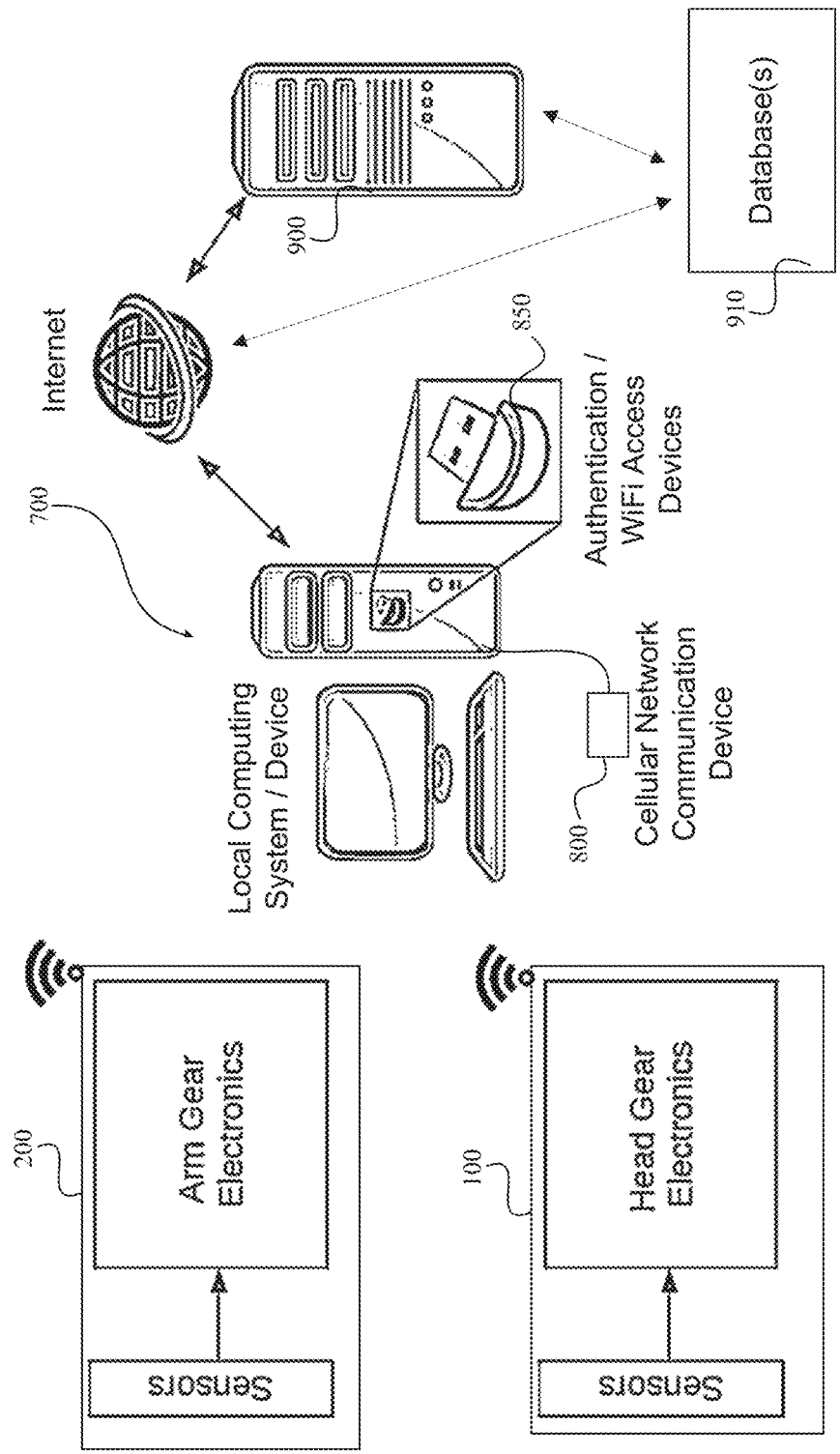
FIG. 1 is a schematic illustration showing portions of a system for facilitating a subject's mind-body and/or mind-body-emotion state self-adjustment/modification/development/maintenance and functional skills development by way of biofeedback and environmental sensing/monitoring in accordance with an embodiment of the present disclosure.

The present disclosure references various representative non-limiting embodiments that are provided for purpose of illustration to aid understanding. In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The use of the term approximately or the recitation of a particular numerical value or value range herein is understood to include or be a recitation of an approximate numerical value or value range, within +/−20%, +/−15%, +/−10%, +/−5%, +/−2.5%, or +/−0% of a stated, measured, baseline, target, or intended value.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

The terms "software," "software resources," "program instructions," and "program instruction sets" herein can correspond or refer to high level and/or low level (e.g., firmware) program instruction resources, routines, procedures, or sequences that are storable in and retrievable from one or more types of information or data storage media, and which are executable by one or more processing units for performing particular types of services, functions, or operations in accordance with embodiments of the present disclosure, in a manner readily understood by individuals having ordinary skill in the relevant art. The term "module" as used herein can typically or primarily correspond or refer to program instruction set or software resources; and the term "unit" as used herein can typically or primarily correspond or refer to hardware resources, and can include associated software resources that support or enable specific types of hardware resource configurations, capabilities, or functions in accordance with embodiments of the present disclosure, in a manner also readily understood by individuals having ordinary skill in the relevant art.

Overview

Embodiments in accordance with the present disclosure are directed to systems, apparatuses, devices, and processes in which a set of signal sensing apparatuses or devices, which can include one or more types of apparatuses or devices worn by or mounted on the body of a subject, user, individual, or patient and possibly one or more types of non-worn or non-bodily mounted apparatuses or devices, are configured for capturing (a) particular types of signals generated internal to a subject's body ("subject internal signals), including physiologic/physiologic correlate signals such as EEG, EMG, and possibly other types of physiologic/physiologic correlate signals (e.g., pulse/heart rate or heart rate variability (HRV) and/or peripheral capillary oxygenation (SpO2) signals); and (b) particular types of signals generated external to the subject's body ("subject external signals"), including movement/motion signals corresponding to subject movements/motions, and environmental signals (e.g., environmental temperature; relative humidity; ambient noise; and/or other types of subject environmental signals such as ambient lighting level; atmospheric pressure and/or altitude; magnetic field intensity; and/or environmental or background electromagnetic radiation levels, such as electromagnetic signal power or energy levels within or across one or more portions of the electromagnetic frequency spectrum, for instance, background microwave and/or radio frequency (RF) signal power or energy levels) corresponding to conditions within the subject's current surroundings or environment. The signal sensing apparatuses carry or include appropriate types of sensing devices or elements (e.g., conventional types of sensing devices or elements) for sensing or capturing such types of signals, in a manner readily understood by individuals having ordinary skill in the relevant art. The signal sensing apparatuses are further configured for communicating or transmitting such captured signals or data corresponding thereto to a local computing system, subsystem, or unit, for instance, by way of wireless communication over a WiFi or similar local wireless network, in a manner also readily understood by individuals having ordinary skill in the relevant art.

Some sensing apparatuses are configured to be carried or worn on particular subject body parts. In multiple embodiments, the set of signal sensing apparatuses includes a head apparatus wearable on the subject's head and configured for sensing EEG signals; and a forearm apparatus wearable on portions of a subject forearm and configured for sensing EMG signals. Depending upon embodiment and/or situational details, the set of signal sensing apparatuses can additionally or alternatively include one or more other types of EMG signal sensing apparatuses, such as a neck apparatus wearable on or around portions of the subject's neck; a chest apparatus wearable on or around portions of the subject's chest/upper torso; a waist/hip apparatus wearable on or around portions of the subject's abdominal, waist, hips, and/or gluteal region(s); an upper leg apparatus wearable on or around portions of a thigh/hamstring region of the subject; or a lower leg apparatus wearable on or around portions of a calf region of the subject. A given subject wearable or subject mountable signal sensing apparatus can carry or include a device or element configured for sensing one or more other types of signals, such as subject heart rate or heart rate variability, and/or possibly peripheral capillary oxygenation (SpO2) level.

Depending upon embodiment details, one or more types of sensing apparatuses or devices configured for capturing or sensing certain types of subject-external signals (e.g., one or more types of ambient environment signals as described above) can remain separate from the subject, and can be carried by or provided as part of the local computing unit, or as apparatuses or devices that are separate from but which are configured for communication with the local communication unit.

The local computing unit is configured for receiving and analyzing signals/data provided, output, or transmitted by the signal sensing apparatuses. In several embodiments, the local computing unit provides or maintains a local wireless network to which the set of sensing apparatuses can link or connect, such as a WiFi or other type of low/generally low power wireless network (e.g., a Bluetooth™ network), such that the sensing apparatuses can communicate sensed subject internal signals and sensed subject external signals to the local computing unit. For instance, the sensing apparatuses can communicate sensed physiologic/physiologic correlate signals/data, sensed subject motion signals/data, and sensed subject environmental signals/data to the local computing unit.

The local computing unit is further configured for generating measures of the subject's current mind state, body state, and possibly emotional state based upon sensed signals/data; providing biofeedback information to the subject relating or corresponding to the subject's current and/or recent mind state measure(s), body state measure(s), and/or emotional state measure(s); and providing/displaying activity or skill development sequences/exercises, mind state training sequences/exercises, body state training sequences/exercises, and possibly emotional state training sequences/exercises in association with the provision of such biofeedback information. More particularly, the local computing unit can be configured for presenting/displaying visual representations of the subject's current mind state, body state, and possibly emotional state as indicated by the subject's current mind state, body state, and emotional state measures. The local computing unit can also be configured for presenting/displaying a visual representation of a target mind state, a target body state, a target emotional state, a target mind-body state, and/or a target mind-body-emotional state that accordingly correspond to a target mind state measure, a target body state measure, and possibly a target emotional state measure, which when concurrently attained or maintained by the subject (e.g., by way of biofeedback based self-regulation) can synergistically enhance or optimize subject performance, skills development/maintenance, wellness, health, and/or well-being. The local computing unit can additionally or alternatively provide a visual/graphical and/or other (e.g., auditory) indication of how far the subject's current mind state, body state, and/or emotional state are away from the target mind state, the target body state, and/or the target emotional state, respectively. The target mind state and target body state can collectively be referred to as a target, balanced, optimized, or synergistic mind-body state, and the corresponding target mind state measure and target body state measure can collectively be referred to as a target, balanced, optimized or synergistic mind-body state measure. Similarly, the target mind state, the target body state, and the target emotional state can collectively be referred to as a target, balanced, optimized, or synergistic mind-body-emotion(al) state, and the corresponding target mind state measure, target body state measure, and emotional state measure can be collectively referred to as a target, balanced, or synergistic mind-body-emotion(al) state measure.

The local computing unit can also concurrently visually present/display representative activity or skill development sequences, mind state training exercises/sequences, body state training exercises/sequences, and possibly emotional state training exercises/sequences in response to subject/user input and/or in an automatically adaptive and dynamic manner based upon the subject's current and/or recent mind state measure(s) body state measure(s), and possibly emotional state measure(s), for instance, relative to the target mind state measure, the target body state measure, and the target emotional state measure, respectively. Activity or skill development sequences can facilitate or be directed to the development or maintenance of particular types of subject activities, skills, or functional abilities such as motor function control during movement sequences, for instance, fine motor function control during potentially complex hand, finger, and wrist movement sequences (e.g., movement sequences involving the manipulation or use of particular types of objects, such as cutlery or chopsticks). Mind state training sequences can facilitate or be directed to the development or maintenance of the target mind state, such as a mind state characterized by concentration in conjunction with relaxed mental awareness. Body state training sequences can facilitate or be directed to the development or maintenance of the target body state, such as a state of muscular relaxation with respect to particular muscles or muscle groups, for instance, between certain agonist and antagonist muscles. Emotional state training sequences can facilitate or be directed to the development or maintenance of the target emotional state, such as a state of rapid heart rate variability recovery in response to an actual or expected stressor or stressful scenario.

Representative manners of determining or calculating mind state measures, body state measures, and synergistic mind state and body state measures, as well as representative manners of adaptively providing or presenting activity/skill development sequences, mind state training sequences, and body state training sequences are described in detail in International Patent Application No. WO/2012161657.

For a given subject during a session in which the set of signal sensing apparatuses worn by the subject are communicating sensed signals/data to the local computing unit and the local computing unit is processing/analyzing such sensed signals/data and providing/displaying corresponding biofeedback information, the local computing unit can additionally generate subject session history information corresponding to at least some of (a) signals/data received from the signal sensing apparatuses; (b) generated mind state measures, body state measures, and possibly emotional state measures; (c) deviations of generated mind state measures, body state measures, and possibly emotion state measures away from the target mind state measure, the target body state measure, and possibly the target emotional state measure; and (d) particular skill development sequences, mind state training sequences, body state training sequences, and possibly emotional state training sequences that were presented/displayed (e.g., in response to user input and/or based upon the user's mind state measures, body state measures, and possibly emotional state measures at one or more times, for instance, relative to the target mind state measure, the target body state measure, and possibly the target emotional state measure respectively). The local computing unit can transmit subject session history information to a set of servers (e.g., a set of remote or cloud-based servers).

The set of servers is configured for analyzing subject session history information received from one or more local computing units, and can further be configured for providing or generating visual/graphical indications of subject progress/performance/skill development over time (e.g., where such information can be accessed, viewed, or used by clinicians/therapists/researchers who are working or associated with one or more subjects). The set of servers can also be configured for generating and/or storing outcome measures that are correlated with or which correspond to an extent (e.g., an estimated or calculated extent) to which an outcome currently attained or realized by a subject (e.g., a "current subject outcome") during subject performance or attempted performance of a functional development activity sequence under consideration matches a target, intended, or ideal example outcome for the functional development activity sequence. For instance, if a functional development activity sequence is directed to manipulating and folding a piece of paper to produce an intended type of origami object, the target example outcome of this functional development activity can be an image of the intended type of origami object that was produced by a skilled, reasonably skilled, and/or unimpaired (e.g., physically and mentally unimpaired) origami practitioner; the current subject outcome can be an image captured of the origami or origami-like object that the subject produced while performing or attempting to perform the functional development activity sequence; and the corresponding outcome measure can be an estimated or calculated extent to which the image of the subject-produced origami or origami-like object matches the image of the intended type of origami object. Such an outcome measure can be produced by way of human comparison, evaluation, and rating of these images, and/or automated (e.g., computerized) image registration, correlation/matching, and scoring techniques known to individuals having ordinary skill in the art.

Additional or other types of target example outcomes can be defined or provided for additional or other types of functional development activity sequences, such as various types of creative skills development sequences (e.g., drawing, painting, singing, or musical instrument playing skills development sequences), vocational skills development sequences (e.g., involving keyboard, calculator keypad, or telephone use; or the manipulation of paper objects, such as for purpose of gift wrapping items purchased by others), and/or activity of daily living (ADL) development sequences (e.g., folding laundry, or turning pages in a book)m in a manner readily understood by individuals having ordinary skill in the relevant art. Individuals having ordinary skill in the relevant art will also recognize that creative skills development sequences, vocational skills development sequences, and ADL development sequences can include or exhibit common categorical types of subject movements or motions (e.g., cross-midline motions or cross-body motions) having applicability to the development or restoration of multiple types of subject skills.

Depending upon the nature of a given functional development activity sequence under consideration, a target example outcome and a current subject outcome for the functional activity development sequence can include image data, audio data, electronic drawing pad and/or electronic stylus data, alphanumeric data (e.g., captured keyboard input), time period or time interval data, accelerometer and/or gyroscope data (e.g., corresponding to one or more accelerometers and/or gyroscopes carried by a subject worn sensing apparatus and/or a device or apparatus (e.g., a non-subject worn device) with which the subject interacts while performing or attempting to perform the functional development activity sequence), pressure mat data (e.g., data generated by a table-top pressure mat during subject performance or attempted performance of functional development activity sequences involving particular types of table-top objects; and/or data generated by a floor-based pressure mat for measuring subject limb motion compensation involving subject application of foot pressure on the floor to move the upper limb, as well measuring floor mat pressure during subject exercises or standing up, which can indicate when and an extent to which the subject unconsciously transfers weight towards the unimpaired side of their body), and/or other types of data or information.

In several embodiments, the set of servers is additionally configured for providing a mind-body-emotional state education, mind-body-emotional state maintenance/regulation, mind-body-emotional state skills development, plus social interaction/social media portal accessible to users, clinicians/therapists/researchers, and possibly other individuals (e.g., user family members or friends). The portal can operate in association with or provide a number of visual/graphical user interfaces by which subject response(s) to one or more types of stresses/stressors/challenges can be estimated, determined, or measured, and measures of subject mind-body-emotional state homeostasis or subject deviation therefrom can be generated, evaluated/analyzed, and presented/displayed.

Representative Aspects of System and Apparatus Embodiments

FIG. 1 is a schematic illustration showing portions of a system 10 for facilitating a subject's mind-body state and/or mind-body-emotion state self-adjustment/modification/development/maintenance and functional skills development (e.g., motor skill development, cognitive skill development, and/or emotional skill development) by way of biofeedback and environmental monitoring in accordance with an embodiment of the present disclosure. In an embodiment, the system 10 includes the following:

(a) a set of signal sensing apparatuses such as (i) a head apparatus 100 that can be worn on the subject's head, and (ii) a forearm apparatus 200 that can be worn on portions of the subject's forearm; (e.g., which can correspond to a functionally impaired arm and/or hand);

(b) a local computing system, apparatus, device, or unit 700 such as a laptop or desktop computer, tablet computer, phablet, and/or mobile telephone, which is configured for communication with each of the head apparatus 100 and the forearm apparatus 200;

(c) possibly or typically an authentication device 800 (e.g., in the form of a dongle) couplable or coupled to the local computing unit 700, which is configured for authenticating and enabling communication between the local computing unit 700 and each of the head apparatus 100 and the forearm apparatus 200, and which in some embodiments includes or is a dongle;

(d) a set of remote servers 900 configured for communication with the local computing unit 700, and configured for communication with a set of databases 910 that can store information related to subjects, including subject histories corresponding to data and/or signals sensed, captured, and/or generated in association with subject interaction with the system; and (e) possibly or typically a server communication/data transfer (e.g., upload) device 850 (e.g., in the form of a dongle) configured for enabling communication/data transfer between the local computing unit 700 and the set of remote servers 900, which in several embodiments includes or is a cellular network communication device or unit (e.g., having at least one subscriber identity module (SIM) card, in a manner readily understood by individuals having ordinary skill in the relevant art).

The set of sensing apparatuses can additionally or alternatively include other types of worn or non-worn apparatuses. For instance, other types of apparatuses that can be worn on particular portions of the user's body include one or more of a neck apparatus, a chest apparatus, a waist/lower back apparatus, and/or a thigh or other type of lower limb apparatus, as further described in detail below.

Each of the head apparatus 100 and the forearm apparatus 200 carries a plurality of sensing devices or elements, including sensing devices/electrodes configured for capturing physiologic/physiologic correlate signals sensed from or produced by the user's body. In several embodiments, the head apparatus 100 and/or the forearm apparatus 200 can carry sensing devices configured for capturing subject-external signals, including environmental signals sensed within and which can characterize the user's current surroundings or environment. Each of the head apparatus 100 and the forearm apparatus 200 also typically carries its own rechargeable power source; a processing unit; a memory; wireless communication circuitry, and wireless recharging circuitry. Aspects of representative head apparatuses 100, forearm apparatuses 200, and other types of user wearable are described in detail hereafter.

Figure 2A:
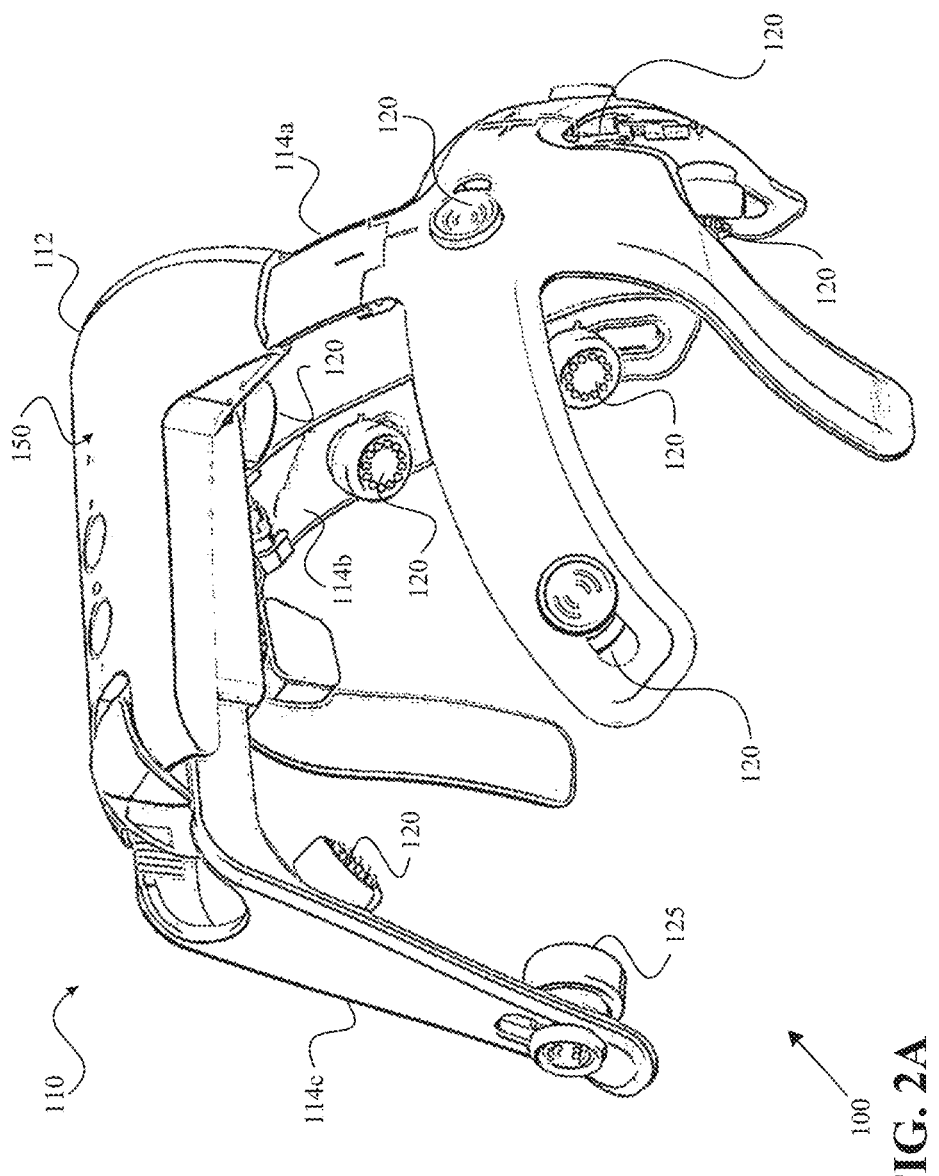
FIG. 2A is a schematic illustrations of a head apparatus in accordance with representative embodiments of the present disclosure.
Figure 2B:
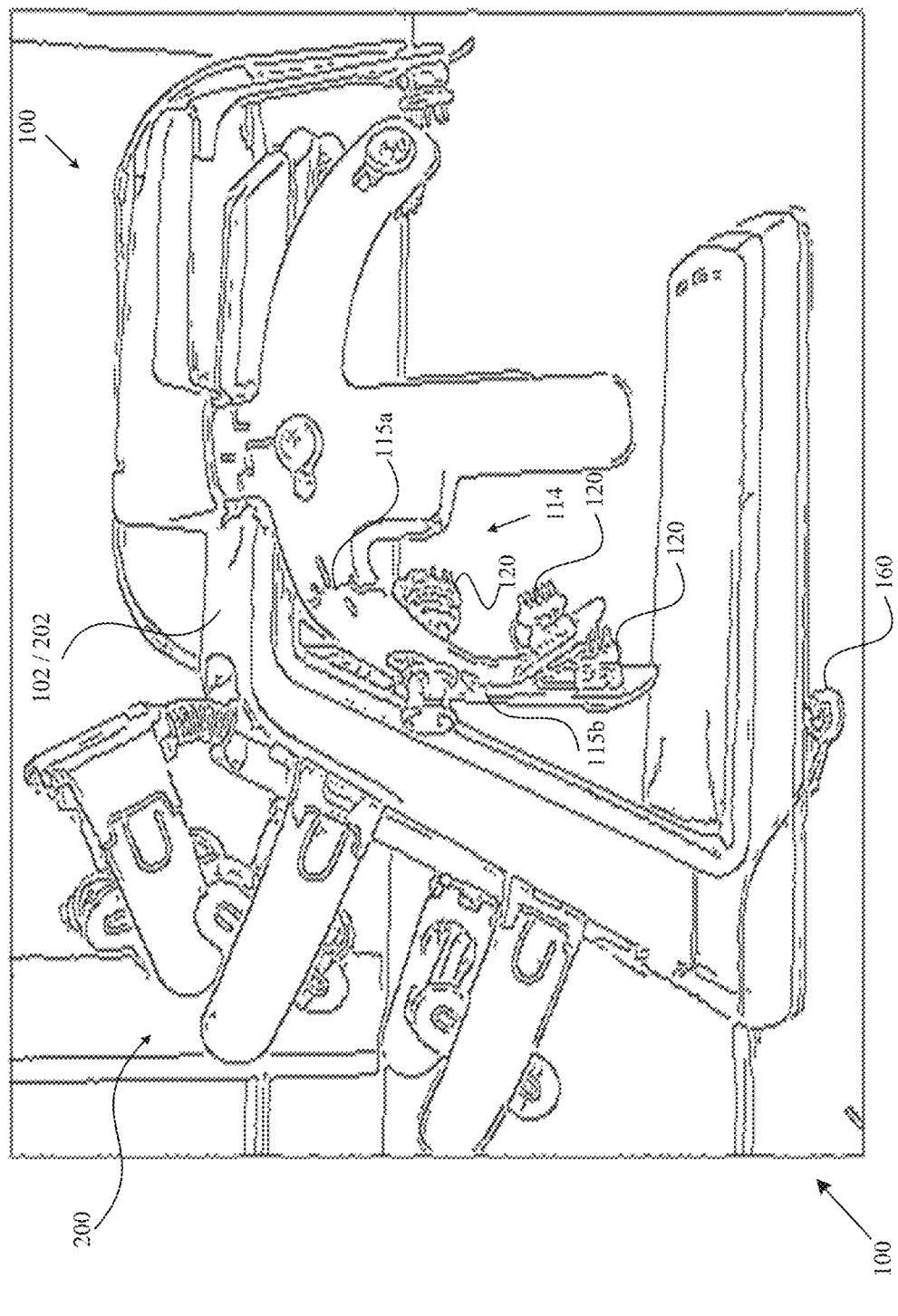
FIG. 2B is a schematic illustration of a recharging receiver or cradle in accordance with an embodiment of the present disclosure, by which a head apparatus and a forearm apparatus can be recharged.

FIG. 2A is a schematic illustration of a head apparatus 100 in accordance with representative embodiments of the present disclosure. FIG. 2B is a schematic illustration of a head apparatus 10 and a forearm apparatus 200 carried by or mounted to a head apparatus/forearm apparatus recharging receiver or cradle 102/202 in accordance with a representative embodiment of the present disclosure.

In an embodiment, a head apparatus 100 includes a lightweight and highly adjustable frame 110 configurable or configured for comfortably yet securely fitting a wide or very wide variety of subject head shapes and sizes. The frame 110 includes a plurality of adjustable arm structures 114 (e.g., three arm structures 114*a-c*, as best shown in FIG. 2A) that extend downwardly and outwardly from a central upper spine portion or structure 112 that carries a head apparatus control/communication unit 150. The arm structures 114*a-c* carry a plurality of EEG electrode structures or electrodes 120 (e.g., dry/gel-free EEG electrodes 120), which in various embodiments are positionable/positioned at locations corresponding or approximately corresponding to particular scalp locations defined in accordance with the standard 10-20 EEG system, in a manner readily understood by individuals having ordinary skill in the relevant art. In several embodiments, at least some arm structures 114 carry at least two hinge structures or hinges 115 (e.g., dual hinges 115*a*, 115*b*), which aid easy, comfortable, consistent placement or mounting of the head apparatus 100 on the subject's head by the subject themselves (e.g., one-handed head apparatus placement or mounting), without external assistance, even for subjects experiencing non-trivial impairment in one of their hands and/or arms.

In a representative implementation, the head apparatus 100 can carry or include EEG electrodes 120 corresponding to positions F3, F4, C3, C4, CZ, P3, P4, O1, and O2 within the standard 10-20 EEG system. The head apparatus 100 can also carry a reference electrode 125 corresponding to the forehead. The EEG electrodes 120 and the reference electrode 125 are independently position-adjustable (e.g., by the subject), and individual EEG electrodes 120 and the reference electrode 125 can be pressure-adjustable (e.g., by the subject). As shown in FIG. 2B, the head apparatus 100 can also carry an ear clip device 160 configured for heart rate sensing or monitoring (e.g., optical pulse/heart rate sensing), in a manner readily understood by individuals having ordinary skill in the relevant art. The head apparatus 100 is configured for simple, rapid, easy adjustment and mounting to the subject's head, including by the subject themselves even when one of the subject's hands/arms is functionally impaired (e.g., as a result of neurologic damage or dysfunction associated with stroke, traumatic brain injury, or another condition).

As also shown in FIG. 2B, the head apparatus 100 can have associated therewith a head apparatus receiver or cradle 102 configured for recharging the head apparatus 100, such as by way of wireless recharging or wireless power transfer. The head apparatus receiver or cradle 102 can be integrated with a forearm apparatus receiver or cradle 202 configured for recharging the forearm apparatus 200, thereby forming the head apparatus/forearm apparatus recharging receiver or cradle 102/202, for instance, in the representative manner shown in FIG. 2B. In a number of embodiments, the head apparatus/forearm apparatus recharging receiver or cradle 102/202 can carry or include thereon or therein the aforementioned server communication/data transfer (e.g., upload and possibly download) device 850, which can be or typically includes or is a cellular network communication device.

The head apparatus EEG electrodes 120, the reference electrode 125, and the ear clip device are coupled to the head apparatus control/communication unit 150, and are respectively configured for communicating EEG signals, a reference electrical signal, and a heart rate signal to the head apparatus control/communication unit 150. The head apparatus control/communication unit 150 includes a power source (e.g., a rechargeable battery, along with recharging circuitry), a processing unit, a memory, sensor/electrode interface circuitry (e.g., analog-to-digital (ADC) conversion circuitry), wireless communication circuitry, and a set of auxiliary sensing devices/elements including a set of motion sensors such as accelerometers and gyroscopes configured for sensing subject movements/motions; plus a set of environmental sensors such as a temperature sensor, a humidity sensor, and a microphone respectively configured for sensing ambient temperature, humidity, and background noise(s) in the subject's environment. By way of the wireless communication circuitry, the head apparatus control/communication unit 150 can transmit sensed EEG signals/data, sensed pulse rate signals/data, sensed user motion signals/data, sensed environmental temperature signals/data, sensed environmental humidity signals/data, and sensed environmental noise/sound signals/data to the local computing unit 700. In various embodiments, the wireless communication circuitry includes or is WiFi communication circuitry.

Figure 3:
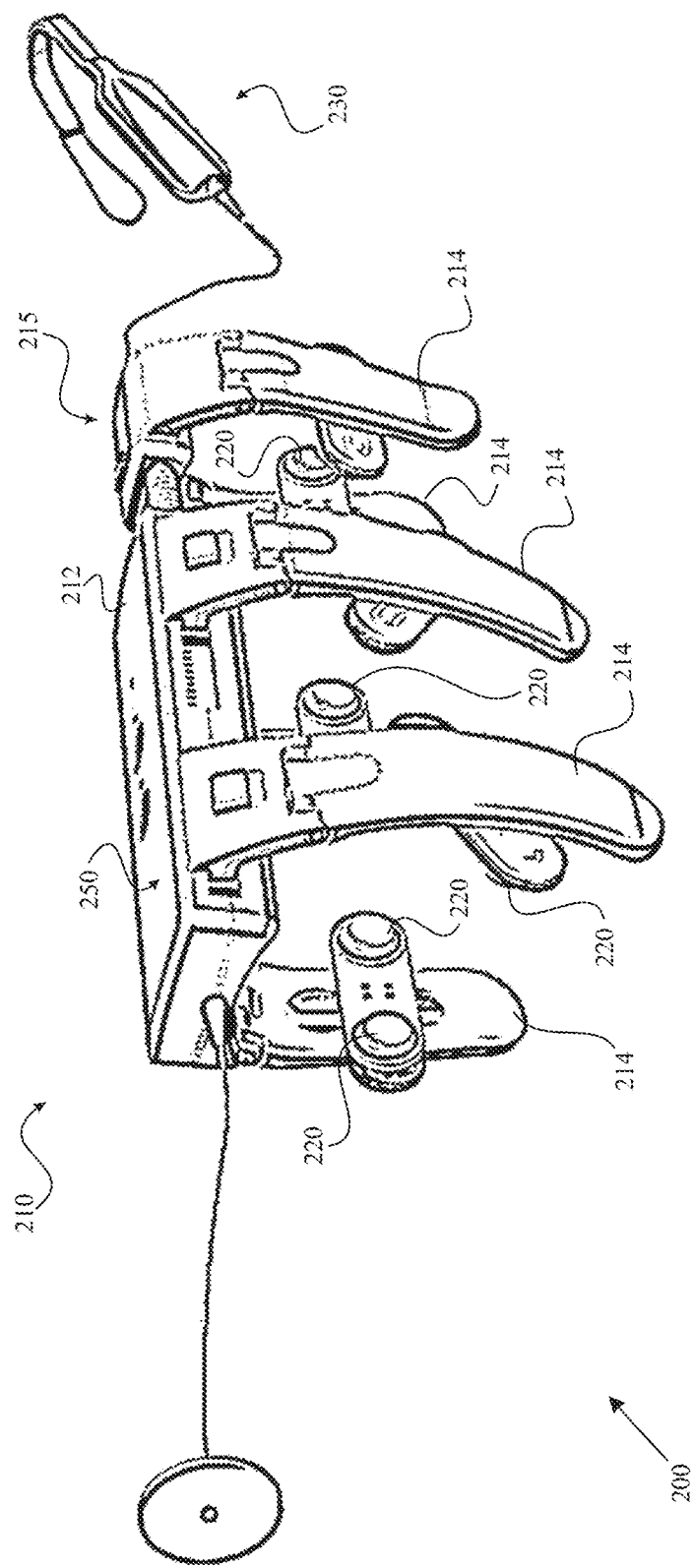
FIG. 3 is a schematic illustration of a forearm apparatus in accordance with a representative embodiment of the present disclosure.

FIG. 3 is a schematic illustration of a forearm apparatus 200 in accordance with a representative embodiment of the present disclosure. In an embodiment, the forearm apparatus 200 includes a lightweight and highly adjustable frame 210 configurable or configured for comfortably yet securely fitting a wide or very wide range of subject forearm lengths and thicknesses. The frame 210 includes a plurality of forearm clip or grip structures 214 that downwardly extend from a central upper spine portion or structure 212 that carries an arm apparatus control/communication unit 250. Each forearm grip structure 212 carries a set of position-adjustable EMG electrode structures or electrodes 220 configured for measuring EMG signals from the subject forearm on which the forearm apparatus 200 is worn. For instance, each forearm grip structure 212 can carry two EMG electrodes 220 having centers or centroids disposed along a common line, where the two EMG electrodes 220 can be pairwise adjusted in vertical and rotational directions relative to the forearm grip structure 212 on which they are carried. The frame 210 can include a front portion 215 that can be selectively extended forward from or retracted rearward toward the upper spine portion 212 in a length-adjustable manner, and from which two forearm clip/grip structures 214 downwardly extend. The forearm apparatus 200 can additionally include a hand clip structure 230, which can be fitted or worn on the subject's palm or hand, and which 230 carries a set of EMG electrodes 220 configured for measuring particular hand muscle EMG signals, such as palm flexor EMG signals. The forearm apparatus 200 is configured for simple, rapid, easy adjustment and mounting to the subject's forearm, including by the subject themselves when one of the subject's hands/arms is functionally impaired (e.g., as a result of neurologic damage or dysfunction associated with stroke, traumatic brain injury, or another condition).

The EMG electrodes 220 are coupled to the forearm apparatus control/communication unit 250, and are configured for communicating sensed EMG signals to the forearm apparatus control/communication unit 250. The forearm apparatus control/communication unit 250 includes a power source (e.g., a rechargeable battery, along with recharging circuitry), a processing unit, a memory, sensor/electrode interface circuitry (e.g., analog-to-digital (ADC) conversion circuitry), wireless communication circuitry, and a set of auxiliary sensing devices/elements including a set of motion sensors such as accelerometers and gyroscopes configured for sensing subject movements/motions; plus a set of environmental sensors such as a temperature sensor, a humidity sensor, and a microphone respectively configured for sensing ambient temperature, humidity, and background noise(s) in the subject's environment. By way of the wireless communication circuitry, the forearm apparatus control/communication unit 250 can transmit sensed EMG data, sensed user motion signals/data, sensed environmental temperature signals/data, sensed environmental humidity signals/data, and sensed environmental noise/sound signals/data to the local computing unit 700. In various embodiments, the wireless communication circuitry includes or is WiFi communication circuitry.

Figure 4A:
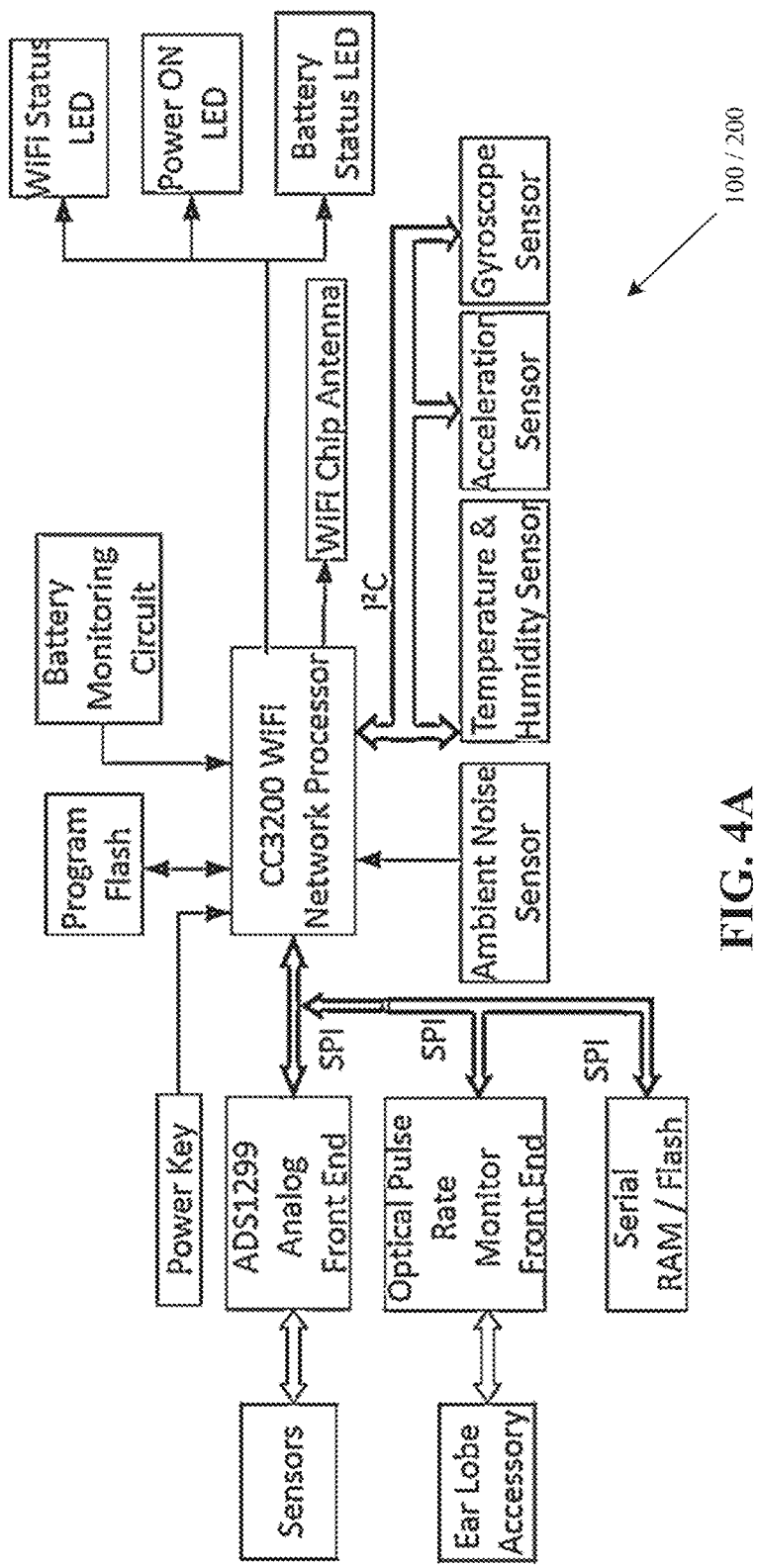
FIG. 4A is an electronics architecture block diagram showing portions of a head apparatus and/or a forearm apparatus in accordance with a representative embodiment of the present disclosure.
Figure 4B:
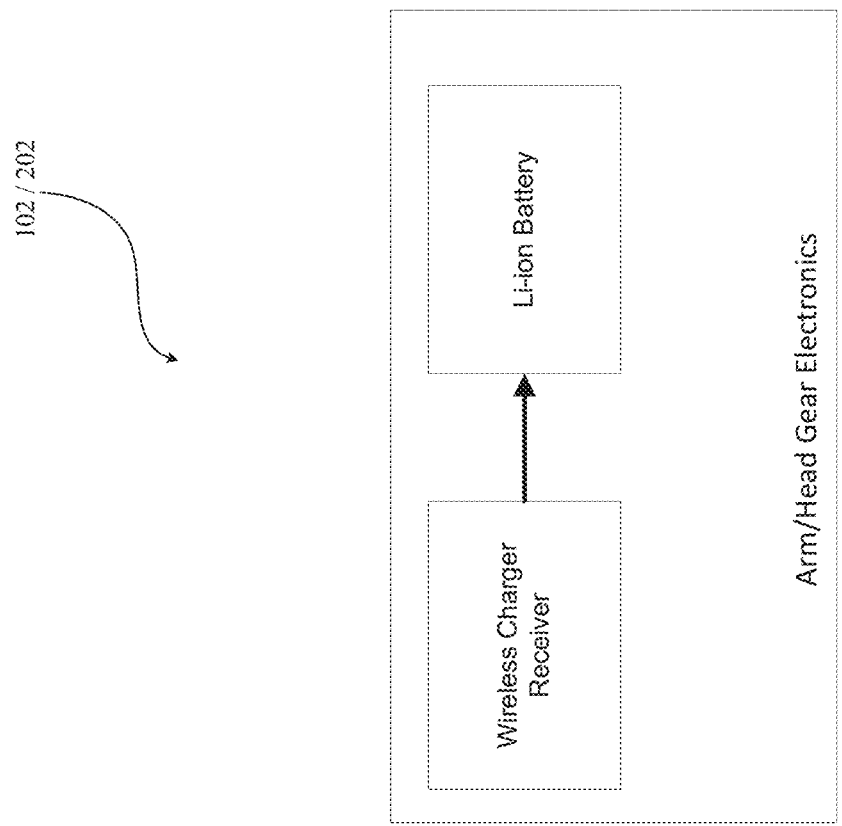
FIG. 4B is a representative (re)charging architecture block diagram showing power source recharging circuitry corresponding to a head apparatus and a forearm apparatus in accordance with a representative embodiment of the present disclosure.
Figure 4B:
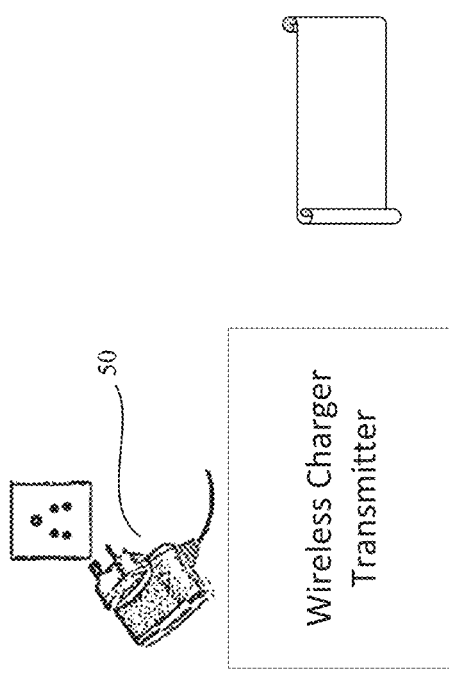

FIG. 4A is an electronics architecture block diagram showing portions of the head apparatus 100 and/or the forearm apparatus 200 in accordance with a representative embodiment of the present disclosure; and FIG. 4B is a (re)charging architecture block diagram showing power source recharging circuitry such as within the head apparatus/forearm apparatus recharging receiver or cradle 102/202 respectively corresponding to the head apparatus 100 and the forearm apparatus 200 in accordance with a representative embodiment of the present disclosure. In multiple embodiments, the system 10 includes a wireless charger transmitter 50 that can be plugged into a wire-based power source such as a conventional electrical socket, and which includes wireless power signal transfer circuitry by which wireless power can be provided to the head apparatus 100 and/or the forearm apparatus 200.

Figure 5:
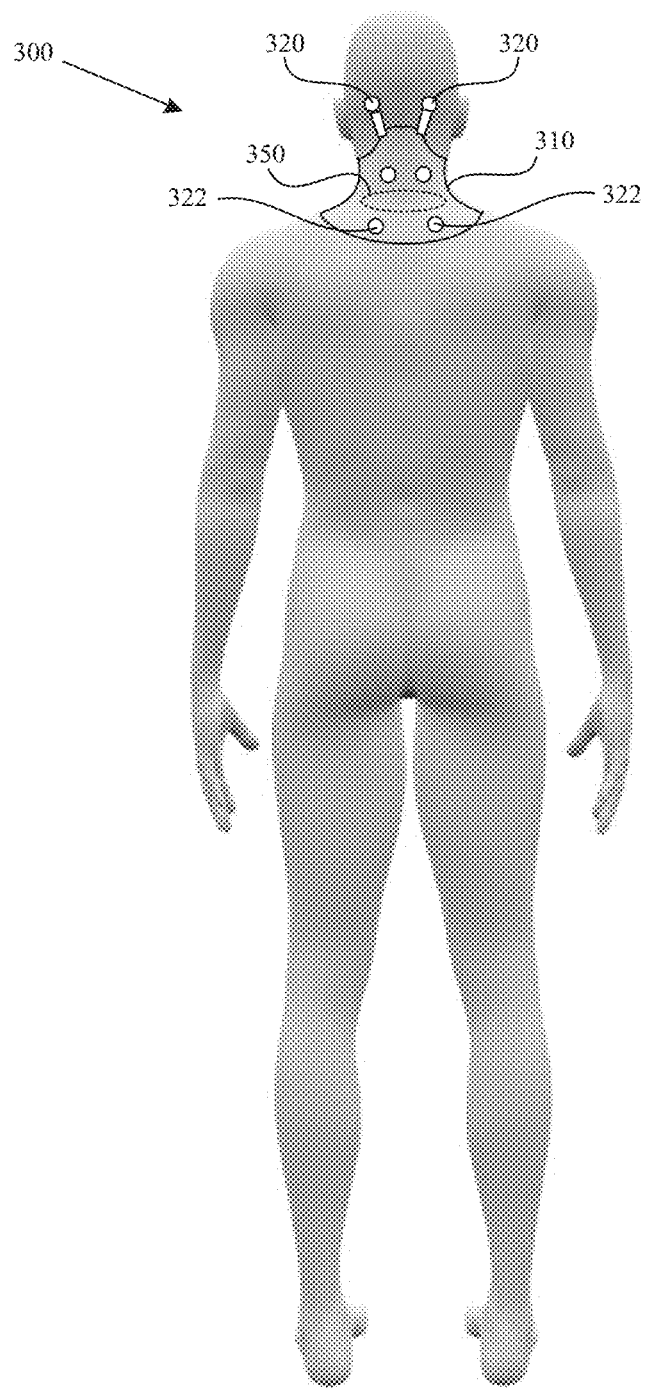
FIG. 5 is a schematic illustration of a neck apparatus configurable or configured for sensing particular EEG signals and particular EMG signals in accordance with an embodiment of the present disclosure.

FIG. 5 is a schematic illustration of a neck mounted or neck apparatus 300 configurable or configured for sensing particular EEG signals and particular EMG signals in accordance with an embodiment of the present disclosure. In an embodiment, the neck apparatus 300 includes a collar structure 310 that surrounds portions of the subject's neck (e.g., side and rear portions of the subject's neck), and which can extend to, along, or around portions of the subject's upper chest region (e.g., the subject's clavicular region). The neck apparatus 300 carries a neck apparatus control/communication unit 350, which is coupled to (a) a set of EEG electrodes 320 (e.g., which can be position adjustable) configured for sensing EEG signals at lower rear portions of the subject's scalp, for instance, corresponding to positions O1 and O2 within the standard 10-20 EEG system; and (b) a set of EMG electrodes 322 (e.g., which can be position adjustable) configured for sending EMG signals corresponding to particular neck/upper torso subject muscles, such as at one or multiple locations of the subject's left and right trapezius muscles. The neck apparatus control/communication unit 350 can further carry a set of auxiliary sensors including a set of motion sensors (e.g., accelerometers/gyroscopes) configured for sensing subject motions/movements and/or tracking subject body position(s); and a set of environmental sensors such as a temperature sensor, a humidity sensor, and an ambient noise sensor in a manner analogous or essentially identical to that previously described. The neck apparatus control/communication unit 350 includes a power source (e.g., a rechargeable battery, along with recharging circuitry), a processing unit, a memory, sensor/electrode interface circuitry (e.g., analog-to-digital (ADC) conversion circuitry), and wireless communication circuitry. By way of the wireless communication circuitry, the neck apparatus control/communication unit 350 can transmit sensed EEG signals/data, sensed EMG signals/data, sensed user motion signals/data, sensed environmental temperature signals/data, sensed environmental humidity signals/data, and sensed environmental noise/sound signals/data to the local computing unit 700. In various embodiments, the wireless communication circuitry includes or is WiFi communication circuitry.

In several embodiments, subject bodily and/or motion signals sensed, detected, estimated, determined, measured, and/or tracked by way of the neck apparatus 300 (e.g., accelerometer and gyroscope signals) can be analyzed by the local computing unit 700 to determine whether the subject's torso/trunk symmetrically rotates or asymmetrically rotates about a longitudinal or lengthwise subject axis (e.g., corresponding or approximately corresponding to the subject's spinal column) during activities, tasks, or exercises in which symmetric torso/trunk rotation is normal or expected (e.g., by a clinician/therapist/researcher). For instance, the local computing unit 700 can estimate, determine, measure, monitor, and/or track an average left-side amount, angular range, or distance across which the subject's left shoulder is displaced during an activity such as walking, and an average right-side amount, angular range, or distance across which the subject's right shoulder is displaced during the activity, where the activity is physically left-right symmetric in nature. A difference between the average left-side shoulder displacement amount, angular range, or distance and the average right-side shoulder displacement amount, angular range, or distance can correspond to or be defined as a torso/trunk rotational asymmetry for the subject. A clinician or therapist can establish a zero asymmetry state (e.g., a state characterized by zero or nearly zero subject torso/trunk rotational asymmetry exists) at one or more times (e.g., prior to every kth session during which the subject interacts or is scheduled to interact with the system 10 to perform or attempt to perform functional activity development sequences) to provide a reference subject torso/trunk state relative to which subject torso/trunk rotational asymmetry is estimated, determined, measured, monitored, and/or tracked.

It has been found by the inventor of the present application that while walking, healthy and/or functionally unimpaired individuals exhibit a shoulder or torso/trunk rotational asymmetry less than or equal to approximately 9 mm (e.g., 9 mm+/−20%, +/−15%, or +/−10%); and unhealthy and/or functionally impaired individuals exhibit a should or torso/trunk rotational asymmetry greater or significantly greater than approximately 9 mm. (e.g., 9 mm+/−20%, +/−15%, or +/−10%) Thus, the extent of subject torso/trunk rotational asymmetry over time can serve as a metric, target value, or threshold value for indicating subject health state and/or subject progress toward or attainment of recovery (e.g., functional recovery from a motor impairment), normalization, health, wellness, and/or well-being.

In addition to or in association with sensing, estimating, determining, measuring, monitoring, or tracking subject torso/trunk rotational asymmetry, the system 10 can be configured for sensing, estimating, determining, measuring, monitoring, or tracking subject torso forward flexion relative to one or both subject legs, as such forward flexion typically accompanies torso/trunk rotational asymmetry.

Figure 6:
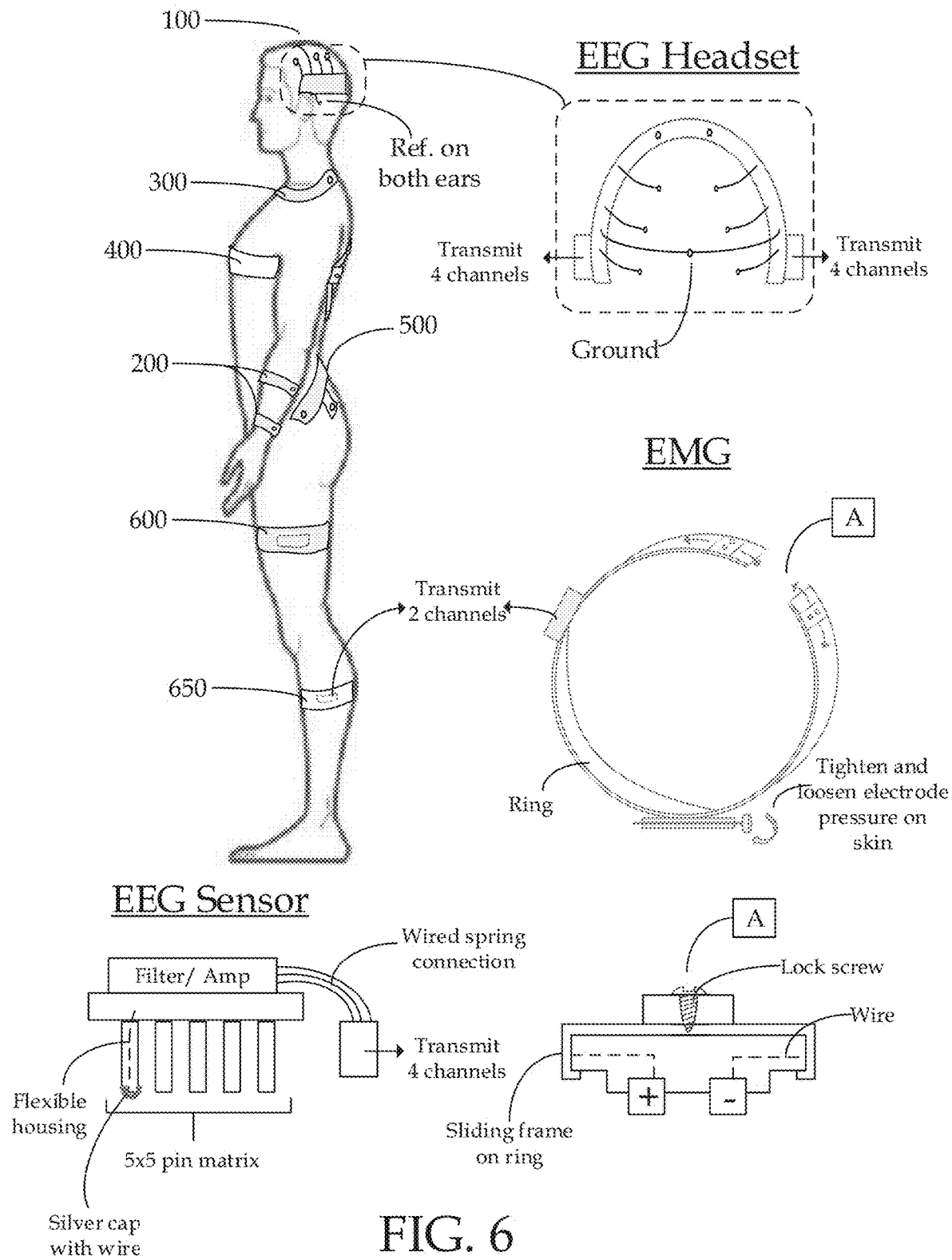
FIG. 6 is a schematic illustration of particular types of body worn sensing apparatuses that can be incorporated into a system in accordance with an embodiment of the present disclosure, in addition or as an alternative to a head apparatus, a forearm apparatus, and/or a neck apparatus.

FIG. 6 is a schematic illustration of other types of body worn sensing apparatuses that can be incorporated into a system 10 in accordance with an embodiment of the present disclosure, in addition to or as an alternative to the head apparatus 100, the forearm apparatus 200, and/or the neck apparatus 300. Such additional/other types of body worn sensing apparatuses can include one or more of a chest apparatus 400; a waist/lower back apparatus 500; an upper leg apparatus 600, and a lower leg apparatus 650, each of which is configured for sensing EMG signals corresponding to particular subject muscles, and possibly sensing subject movements and/or environmental parameters such as temperature, humidity, and ambient noise, in a manner analogous or essentially identical to that described above. Each of such additional/other types of body worn sensing apparatuses 400, 500, 600, 650 can further be configured for wirelessly communicating sensed signals/data to the local computing unit 700, in a manner also analogous or essentially identical to that described above, as will be readily understood by individuals having ordinary skill in the relevant art.

Figure 7:
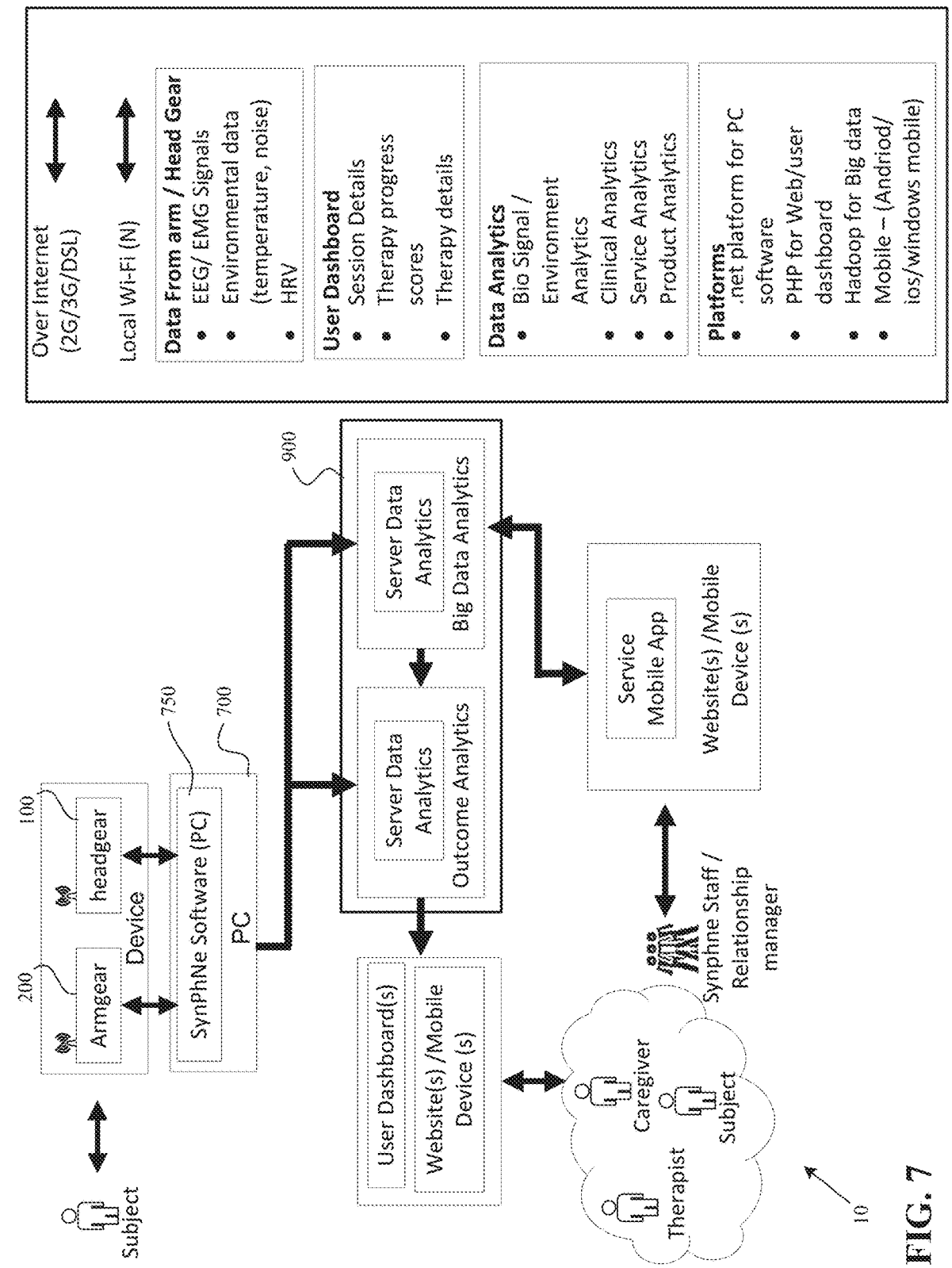
FIG. 7 is a schematic illustration showing further aspects of a system in accordance with an embodiment of the present disclosure, including sensing apparatuses that can wirelessly communicate sensed signals/data to a local computing unit by way of an authentication unit.

FIG. 7 is a schematic illustration showing further aspects of a system 10 in accordance with an embodiment of the present disclosure. With reference also to FIGS. 1-6, the set of user worn sensing apparatuses, such as the head apparatus 100, the forearm apparatus 200, and/or another sensing apparatus 300, 400, 500, 600, 650 can wirelessly communicate sensed signals/data to the local computing unit 700 by way of an authentication unit 800 coupled to the local computing unit 700, as indicated in FIG. 1. The authentication unit 800 can include or be, for instance, a dongle configured for supporting or enabling WiFi and/or Bluetooth™ communication, and which can also be configured for supporting or enabling sensing device authentication operations.

The local computing unit 700 provides software resources 750 (e.g., program instruction sets) configured for supporting, enabling, and/or providing one or more types of local computing unit capabilities, services, or functions described above, including the processing/analysis of data received from the set of sensing apparatuses. The local computing unit 700 can transmit or upload the aforementioned subject session history information to the set of servers 900, such as by way of the server communication/data transfer device 850. In several embodiments, the server communication/data transfer device 850 is configured for cellular network data communication with the set of servers 900, for instance, by way of one or more of a 2G, 3G, or 4G cellular network communication protocol. The server communication/data transfer device 850 can additionally or alternatively be configured for one or more other types of data communication with the set of servers, such as by way of a conventional wire-based network coupling, link, or connection. In general, the local computing unit 700 and/or the server communication/data transfer device 850 are configurable or configured for providing automatic and enhanced reliability communication with the set of servers 900, for instance, when the local computing unit 700 does not have a reliable wire-based Internet connection; or when the local computing unit 700 is a portable/laptop computer that is in-transit between different locations between subject sessions, during which case subject session information can be automatically communicated to the set of servers 900 while the local computing unit 700 is in-transit.

In various embodiments, the local computing unit 700 includes program instructions that when executed by a processing unit automatically initiate and manage the wireless communication or transfer of information or data between the local computing unit 700 and the set of servers 900 by way of the server communication/data transfer device 850, independent of or without subject initiation, management, or termination of such information or data communication or transfer. For instance, after a subject has completed a session involving subject performance or attempted performance of one or more functional activity development sequences, the local computing unit 700 can automatically, without requiring subject input, instruction, or acknowledgment, automatically communicate session related data (e.g., subject mind state measures, body state measures, possibly emotional state measures, functional activity sequence performance data, and possibly one or more current subject outcome measures for the functional development activity sequence or sequences under consideration) to the servers 900. Additionally, in several embodiments, the servers 900 can automatically communicate information or data to the local computing unit 700 by way of the server communication/data transfer device 850, without requiring subject input, instruction, or acknowledgment. Such data can include new or updated functional development activity sequence information, software upgrades, and other information.

The set of servers 900 stores and processes/analyzes subject session information received from local computing units 700, and generate analytics information/data therefrom, based upon one or more sessions corresponding to one or more subjects. The set of servers 900 can generate various types of analytics information, including physiological signal analytics; motion signal analytics; environmental signal analytics; sensing apparatus analytics; mind state analytics; body state analytics; skill, activity, or exercise sequence analytics; and/or other types of analytics corresponding to single subjects or groups of subjects. Based upon the generated analytics information, the set of servers can provide particular types of analytics capabilities, services, or functions to clinicians, therapists, researchers, medical insurance company personnel, marketing personnel, and/or other individuals, including subjects themselves. Analytics information, as well as other information such as current and historical subject mind state measures, body state measures, emotional state measures, subject outcome measures, subject body rotation measures, subject responses to stimuli such as stressors or stressful scenarios, and target outcome measures can be stored in a set of databases 910 with which the server(s) 900 can communicate.

Environmental analytics can be important or very important because environmental factors to which a subject is exposed during a session such as ambient or background temperature, humidity level, noise level, types of noise(s), and/or other environmental metrics (e.g., ambient or background lighting level, atmospheric pressure or altitude level, magnetic field intensity, and/or electromagnetic radiation or energy level(s) in one or more electromagnetic signal frequency bands, such as one or more microwave and/or RF signal frequency bands) can significantly or greatly affect the subject's mind state, body state, emotional state, responsiveness to biofeedback, ability to self-regulate to attain the target or synergistic mind-body state or mind-body-emotion state, and ability to develop, improve, or maintain functional abilities or skills associated with activity/skill development sequences. Environmental analysis can aid clinician/therapist/researcher determination of what types of environmental conditions facilitate enhanced subject performance for any given subject, and why subject performance or performance improvement is not at an expected level, or fluctuates, degrades, or plateaus in an undesirable/unpredictable manner from one session to another or during a given session.

The set of servers 900 can communicate with one or more websites and/or mobile apps that can provide visual/graphical user interfaces by which system support personnel, therapists/clinicians/researchers, and other individuals such as subjects can selectively access and/or view analytics information.

Furthermore, in various embodiments, the set of servers 900 can provide or support a mind-body-emotion state education, mind-body-emotion state maintenance/regulation, mind-body-emotion state skills development, and social interaction/social media portal accessible to users, clinicians/therapists/researchers, and possibly other individuals (e.g., user family members or friends). The portal can operate in association with or provide a number of visual/graphical user interfaces by which EEG and EMG based subject bio-markers can be measured; subject response(s) to particular types of stresses/stressors/challenges can be estimated, determined, or measured; and indications or measures of subject mind-body-emotion state can be generated, evaluated/analyzed, and presented/displayed. Such subject mind-body-emotion state indications or measures can convey (e.g., visually) how far away the subject's current/recent mind-body-emotion state is from a target, synergistic, or homeostasis mind-body-emotion state that can enhance or optimize the subject's performance, health, wellness, and well-being. Such visual/graphical user interfaces can aid subject awareness and self-regulation of their own stress response(s) and their mind-body-emotion state over time by way of biofeedback, thereby progressively aiding or enhancing subject performance, health, wellness, and well-being over time.

In various embodiments, the set of servers 900 can receive information provided, output, or generated by one or more types of subject sensing apparatuses such as the neck apparatus 300 and/or the head apparatus 100, the forearm apparatus 200, and/or another sensing apparatus in order to obtain subject mind-body-emotion state related bio-marker signals, data, or measurements that facilitate the estimation, determination, measurement, analysis, and/or biofeedback based self-regulation of subject mind-body-emotion state. Such bio-marker measurements include at least some of the following:

(a) EEG bio-markers: alpha, beta, and delta frequency band EEG signal measurements including band power, overall EEG power, EEG hemispheric asymmetry, and EEG signal recovery time in response to stress/challenge;

(b) EMG biomarkers: resting and induced relaxation EMG signal measurements, subject activity baseline measurements, maximum voluntary contraction (MVC) measurements, EMG signal recovery time in response to stress/challenge, and left-right muscle tension asymmetry;

(c) Heart Rate Variability (HRV) signals, and HRV signal recovery time in response to stress/challenge (d) possibly SpO2;

(e) relaxation resistance; and (f) stress/challenge recovery profile measurements, as further detailed hereafter.

Measurement of the subject's stress/challenge recovery profile can include measurement of one or more psychological/emotional stress recovery profiles, and/or measurement of one or more physical stress recovery profiles. In various embodiments, measurement of a psychological/emotional stress recovery profile involves measurement of subject EEG signals or bio-markers, measurement of subject EMG signals or bio-markers, and measurement of subject HRV signals during the presentation/display of an auditory-visual scene or video (e.g., which can be stored on and obtained from the set of databases 910) that includes one or more expected stressful, psychologically/emotionally challenging, surprising, and/or unexpected scenes, situations, or scenarios therein. Prior to subject viewing or exposure to a psychologically stressful or expected stressful scene, the subject's mind state as indicated by their EEG signals or bio-markers, body state as indicated by their EMG signals or bio-markers, and emotional state as indicated by their HRV signals can be respectively defined to correspond to or represent a baseline or non-stressed/non-challenged mind state, body state, and emotional state.

When the subject is exposed to or views a stressful, surprising, or unexpected scene or situation presented in the video, the subject's mind state as indicated by their EEG signals or bio-markers, body state as indicated by their EMG signals or bio-markers, and emotional state as indicated by their HRV signals can shift, significantly shift, or dramatically shift away from the respective baseline or non-stressed states. Such shifts can be defined as a psychological/emotional stress response for the subject, which includes a mind state stress response component, a body state stress response component, and an emotional state stress response component. Following subject exposure to the stressful scenario or scene (e.g., when the video has returned to or resumed presenting non-stressful or ordinary scenes), the subject's mind state as indicated by their EEG signals or bio-markers, body state as indicated by their EMG signals or bio-markers, and emotional state as indicated by their HRV signals will respectively shift or return towards the baseline or non-stressed mind state, body state, and emotional state.

Multiple embodiments in accordance with the present disclosure can monitor, estimate, determine, or measure the time taken for each of the subject's mind state (as indicated by EEG signals or bio-markers), body state (as indicated by EMG signals or bio-markers), and emotional state (as indicated by HRV signals) to respectively return to or approximately (re)attain (e.g., within 10-20%) the baseline or non-stressed mind state, body state, and emotional state, respectively, following the initiation or cessation of a psychological/emotional stressor such as a stressful video scene. Such times can correspondingly be defined as mind state recovery time, a body state recovery time, and an emotional state recovery time associated with subject exposure to the psychological/emotional stressor (e.g., the stressful video scene). Such embodiments can additionally or alternatively determine a mind state recovery profile, a body state recovery profile, and/or an emotional state recovery profile that indicate a pattern (e.g., as defined by a temporal sequence of mind state measure values, body state measure values, and/or emotional state value measures) by which the subject's mind state, body state, and/or emotional state recover toward the baseline mind state, the baseline body state, and the baseline emotional state, respectively.

It has been found by the inventor of the present application that for healthy and/or functionally unimpaired subjects, their mind state stress response component, body state stress response component, and emotional state stress response component return quickly and nearly simultaneously to, or approximately to, the respective baseline or non-stressed mind state, body state, and emotional state, and typically in a smooth decreasing manner with respect to the values of the subject's mind state measures, body state measures, and emotional state measures over time. However, for functionally impaired or unhealthy individuals, the return of one or more of their mind state stress response component, body state stress response component, and emotional state stress response component to or approximately to the baseline or non-stressed mind state, body state, and emotional state is delayed compared to healthy and/or functionally unimpaired subjects, and the recovery profile of the subject's stressed mind state, body state, and/or emotional state return toward their respective baseline states or levels can be irregular or very irregular (e.g., showing significant or large bidirectional changes, rather than smooth decay). Thus, single instance and/or historical manner(s) in which and/or temporal durations across which a subject's mind state stress response component, body state stress response component, and emotional state stress response component return or approximately return to the baseline or non-stressed mind state, the baseline or non-stressed body state, and the baseline or non-stressed emotional state following (initial) exposure of the subject to a psychological/emotional stressor can serve as a measure of subject performance, progress, recovery (e.g., functional recovery, for instance, from a motor impairment), normalization, health, wellness, or well-being.

In an analogous or generally analogous manner, in various embodiments measurement of a physical stress recovery profile involves measurement of subject EEG signals or bio-markers, measurement of subject EMG signals or bio-markers, and measurement of subject HRV signals during subject engagement or attempted engagement in a particular type of stressful or challenging activity, task, or exercise (e.g., a physically stressful or challenging activity or task, involving subject positioning/attempted positioning and/or maintenance of one or more of their body parts in a given physical pose or orientation, for instance, a yoga position such as a plank pose; or subject engagement or attempted engagement in a creative activity such as an artistic, craft, theater, dance, or musical activity). Prior to subject engagement in the stressful activity or activities, the subject's mind state as indicated by their EEG signals or bio-markers, body state as indicated by their EMG signals or bio-markers, and emotional state as indicated by their HRV signals can be respectively defined to correspond to or represent a baseline or non-stressed/non-challenged mind state, body state, and emotional state with respect to a physically stressful activity.

When the subject is engaged in a physically stressful activity, the subject's mind state as indicated by their EEG signals or bio-markers, body state as indicated by their EMG signals or bio-markers, and emotional state as indicated by their HRV signals can shift, significantly shift, or dramatically shift away from the respective baseline or non-stressed states. Such shifts can be defined as a physical stress response for the subject, which includes a mind state stress response component, a body state stress response component, and an emotional state stress response component. Following subject engagement in the physically stressful activity, subject mind state as indicated by their EEG signals or bio-markers, body state as indicated by their EMG signals or bio-markers, and emotional state as indicated by their HRV signals will respectively shift or return towards the baseline or non-stressed mind state, body state, and emotional state.

Multiple embodiments in accordance with the present disclosure can monitor, estimate, determine, or measure the time taken for each of the subject's mind state (as indicated by EEG signals or bio-markers), body state (as indicated by EMG signals or bio-markers), and emotional state (as indicated by HRV signals) to respectively return to or approximately (re)attain (e.g., within 10-20%) the baseline or non-stressed mind state, body state, and emotional state, respectively, following cessation of the physically stressful activity. Such times can correspondingly be defined as mind state recovery time, a body state recovery time, and an emotional state recovery time associated with subject exposure to a physical stressor. Additionally or alternatively, multiple embodiments in accordance with the present disclosure can determine recovery profiles by which the subject's mind state, body state, and/or emotional state return or approximately return to their respective baseline states.

It has been found by the inventor named on the present application that for healthy and/or functionally unimpaired subjects, their mind state stress response component, body state stress response component, and emotional state stress response component return quickly and nearly simultaneously to, or approximately to, the respective baseline or non-stressed mind state, body state, and emotional state after cessation of the physical stressor. Also, the mind state, body state, and emotional state recovery profiles for healthy and/or functionally unimpaired subjects are typically characterized by smooth decay. However, for functionally impaired or unhealthy individuals, the return of one or more of their mind state stress response component, body state stress response component, and emotional state stress response component to or approximately to the baseline or non-stressed mind state, body state, and emotional state is delayed compared to healthy and/or functionally unimpaired subjects; and/or the mind state recovery profile, body state recovery profile, and/or emotional state recovery profile of an impaired or unhealthy subject can exhibit irregular patterns or significant swings (rather than smooth decay) as the subject's mind state, body state, and emotional state return toward their respective baseline states. Thus, single instance and/or historical manner(s) in which and/or temporal durations across which a subject's mind state stress response component, body state stress response component, and emotional state stress response component return or approximately return to the baseline or non-stressed mind state, the baseline or non-stressed body state, and the baseline or non-stressed emotional state following cessation of a physical stressor can serve as a measure of subject performance, progress, recovery (e.g., functional recovery, for instance, from motor impairment), normalization, health, wellness, or well-being.

In a number of embodiments, the set of servers 900 is configured for communicating with one or more types of electronic/computing devices, for instance, portable/mobile subject devices such as smartphones, tablet/phablet computers, laptop computers, and/or desktop computers, such that the electronic/computing device(s) can present visual/graphical user interfaces that facilitate or enable the capture, generation, and/or communication of the aforementioned subject bio-marker information and the generation and presentation of subject mind-body-emotion state information corresponding thereto. Such electronic/computing devices can include or be clinician/therapist/researcher devices, and/or subject devices, which are configured for communicating with one or more types of subject signal sensing apparatuses 100, 200, 300, 400, 500, 600, 650 worn by subjects. In embodiments in which the set of servers 900 communicates with portable/mobile devices such as smartphones, each portable/mobile device can execute a mobile app that facilitates or enables the collection, generation, and/or presentation of subject bio-marker measurements and/or subject mind-body-emotion state information.

In various embodiments, the foregoing bio-marker measurements can be used to generate brain-body-emotion or mind-body-emotion state information, such as by way of a visual/graphical user interface. This mind-body-emotion state information can be referred to as Guna state information or composite mind-body-emotion state information. Different categorical types of Guna state or composite mind-body-emotion state information can be defined, for instance, in a representative manner shown in FIG. 10, e.g., by way of a visual or graphical table 1410 provided in a visual or graphical composite mind-body-emotion state interface 1400. Depending upon a subject's current/recent (a) mind or brain state determined from or indicated by EEG bio-markers; (b) body state determined from or indicated by EMG bio-markers; and (c) emotional state as determined from or indicated by HRV, the subject's current composite mind-body-emotion state can be categorized in the manner indicated by each row of FIG. 10. A target, optimal, or ideal composite mind-body-emotion state is indicated in the last row of FIG. 10, which can be defined as a target, synergistic, well-balanced, or homeostasis mind-body state that the subject should attain and maintain or which the subject should shift or progress towards in order for enhancing or maximizing their performance, health, wellness, and/or well-being with respect to any given activity in which they are engaged. The subject's current or most-recent composite mind-body-emotion state can be visually or indicated by way of graphical objects such as selectively colored graphical buttons (e.g., red buttons indicating the subject's current composite mind-body-emotion state).

Figure 8A:
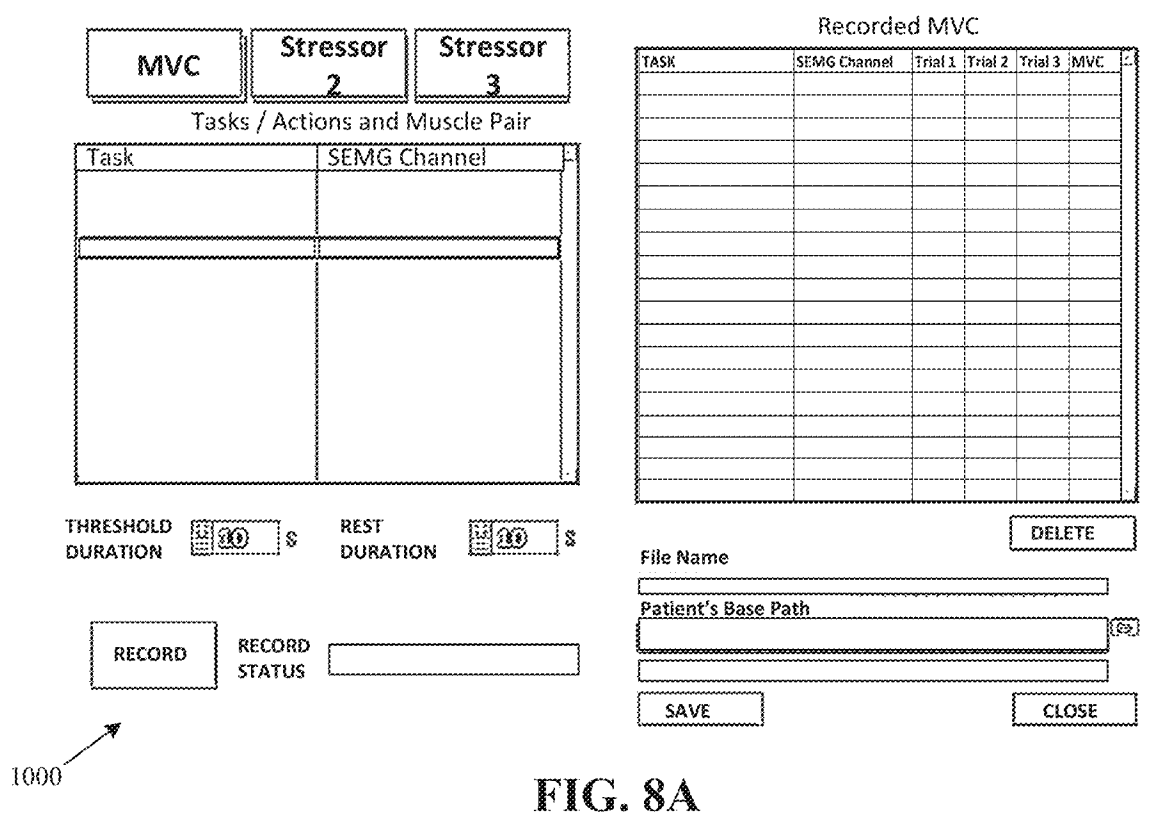
Figure 8B:
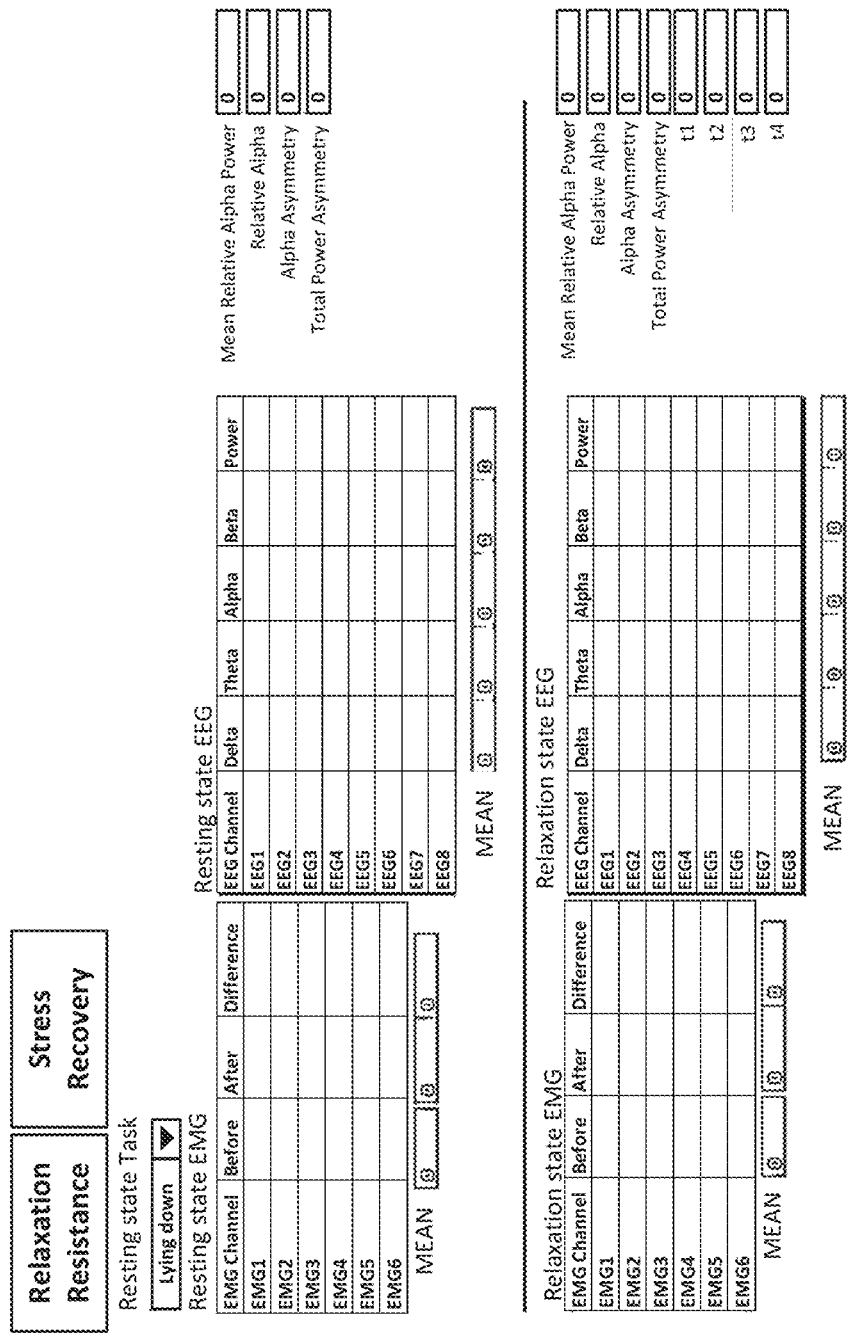
Figure 8C:
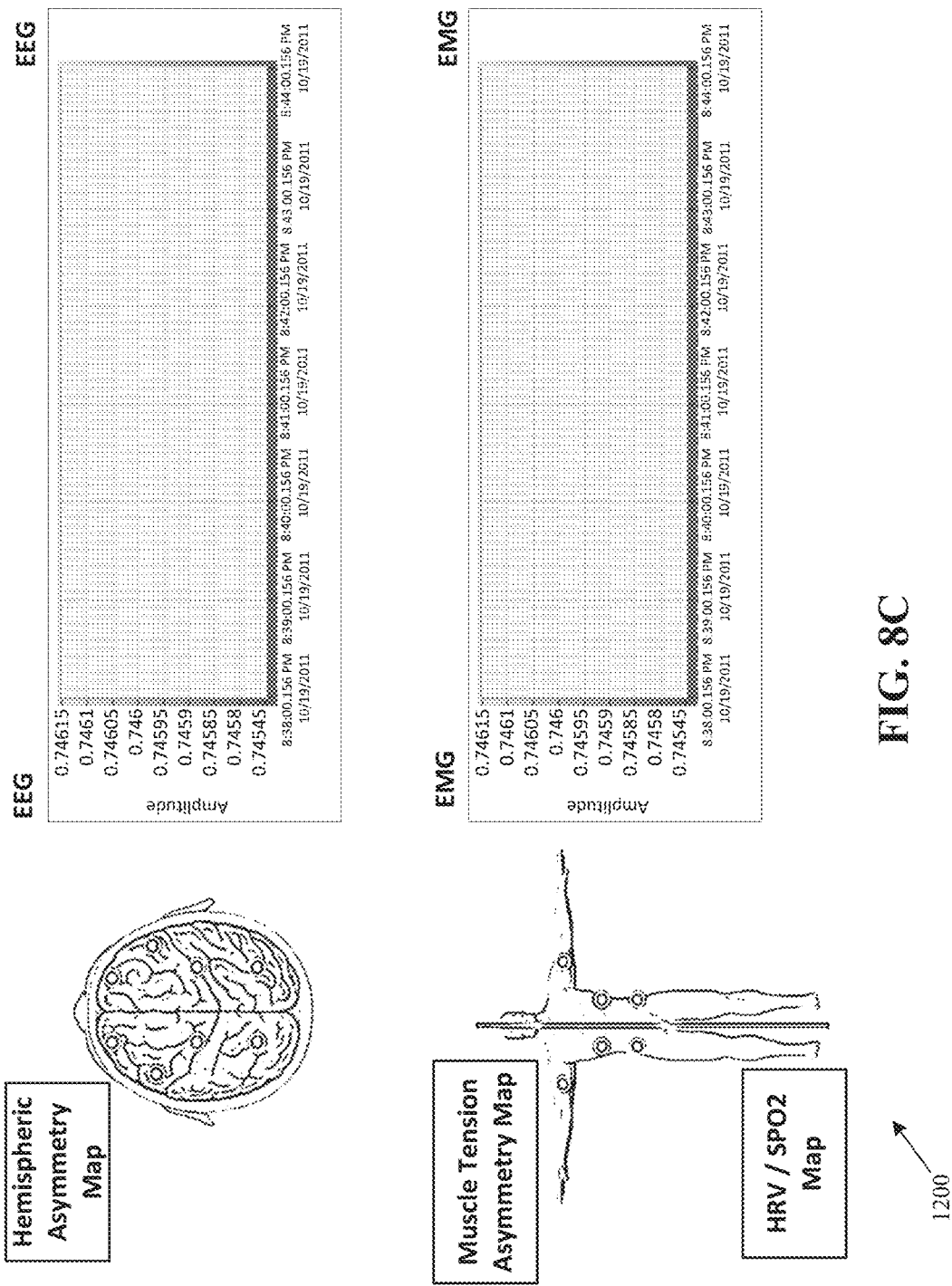

FIGS. 8A-8C are representative visual interfaces 1000, 1100, 1200 that a system 10 in accordance with an embodiment of the present disclosure can provide to clinicians/therapists/researchers and possibly the subject in order to facilitate or enable measurement or generation of the foregoing subject mind-body and/or mind-body-emotion related bio-markers, and visualization of results corresponding thereto. Such visual interfaces 1200 can provide one or more types of indications of EEG hemispheric asymmetry and EMG based left-right muscular tension asymmetry.

Figure 9:
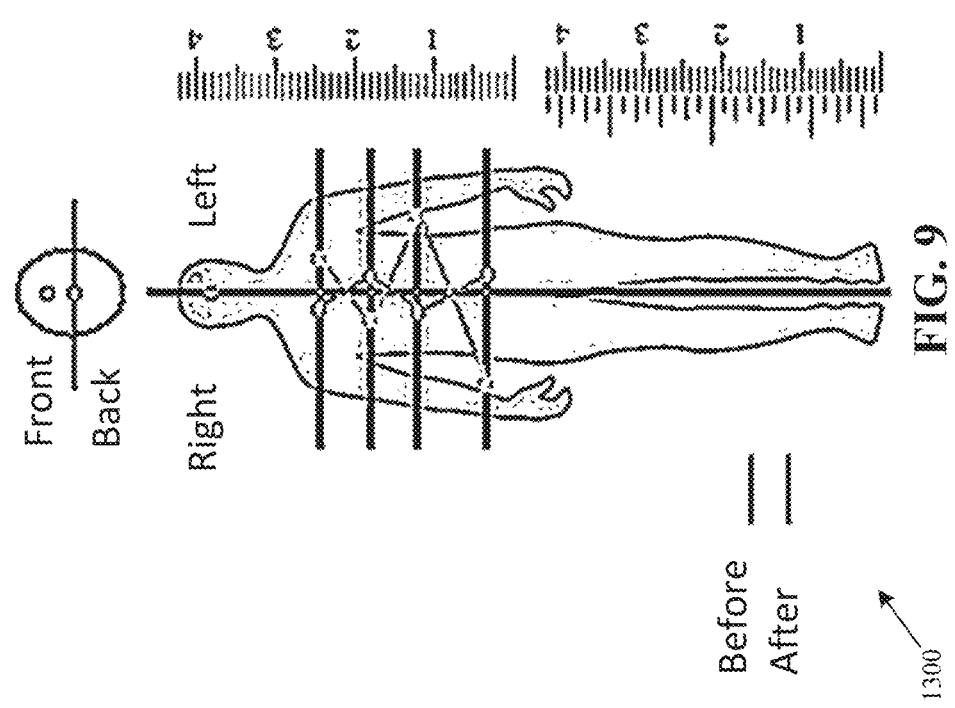
FIG. 9 is a representative visual interface that a system in accordance with an embodiment of the present disclosure can provide as or as a part of a biofeedback interface to indicate a subject's current or recent level(s) of brain hemisphere EEG asymmetry and left-right muscle tension asymmetry.

FIG. 9 is a representative visual interface 1300 that a system 10 in accordance with an embodiment of the present disclosure can provide to a subject and/or other individuals (e.g., clinicians or researchers), for instance, as or as a part of a biofeedback interface to indicate the subject's current or recent level(s) of brain hemisphere EEG asymmetry and left-right muscle tension asymmetry, such that the subject can self-regulate their mind state and body state in order to shift their EEG profile towards or to a state of hemispheric symmetry and shift their muscle tension profile towards or to a state of balanced left-right muscle relaxation by way of biofeedback (e.g., as a result of the subject becoming consciously aware of their current level of hemispheric symmetry/asymmetry and left-right muscle tension or relaxation symmetry/asymmetry). Such a visual interface 1300 can additionally provide a visual indication of the subject's HRV, for instance, relative to a target HRV level or range that corresponds to mind-body-emotion state homeostasis.

Aspects of particular embodiments of the present disclosure address at least one aspect, problem, limitation, and/or disadvantage associated with existing systems, apparatuses, devices, and techniques for providing biofeedback and developing or restoring subject skills such as movement control, including fine motor control. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of this disclosure. It will be appreciated by a person of ordinary skill in the art that several of the above-disclosed systems, components, processes, or alternatives thereof, may be desirably combined into other different systems, components, processes, and/or applications. In addition, a person of ordinary skill in the art may make various modifications, alterations, and/or improvements to one or more embodiments herein while remaining within the scope of the present disclosure.

The invention claimed is:

1. A computerized method for treating a human subject with an impaired function due to neurological damage through the development of physical, mental and emotional skills, the method comprising:
   fitting the subject with a sensor device having sensors for continuously sensing subject-internal signals during a treatment session;
   receiving, by a processor, the sensed subject-internal signals including physiologic signals from the sensor device;
   continuously calculating on a real-time basis during the treatment session by the processor,
      a current subject mind state measure based on neural activity signals of the received subject-internal signals, a current subject body state measure based on muscle activity signals of the received subject-internal signals, and a current subject emotional state measure based on heart rate variability signals of the received subject-internal signals;

administering by the processor during the treatment session a set of functional development activity sequence or training exercises for the subject to perform depending on the continuously calculated current subject mind state measure, current subject body state measure and current subject emotional state measure, wherein administering comprises displaying on the user interface the set of functional development activity sequence targeted to rehabilitate the impaired function of the subject when
the continuously calculated current subject body state measure is at the target body state measure,
the continuously calculated current subject mind state measure is at the target mind state, and
the continuously calculated current subject emotional state is at the target emotional state, displaying on the user interface mind state training exercises when the continuously calculated current subject mind state is not at the target mind state to direct the continuously calculated current subject mind state to the target mind state, displaying on the user interface body state training exercises when the continuously calculated current subject body state is not at the target body state to direct the continuously calculated current subject body state measure to the target body state, displaying on the user interface emotional state training exercises when the continuously calculated subject emotional state is not at the target emotional state to direct the continuously calculated current subject emotional state to the target emotional state, and wherein performing the set of functional development activity sequence when the continuously calculated current subject mind state, continuously calculated current subject body state and continuously calculated current subject emotional state are at the target mind state, target body state and target emotional state optimizes the subject's performance to improve recovery of the impaired function, determining a health state of the subject comprising
determining at least one of,
a session mind state recovery profile comprising a session mind state measure recovery pattern as it returns towards baseline subject mind state,
a session body state recovery profile comprising a session body state measure recovery pattern as it returns towards a baseline subject body state,
a session emotional state recovery profile comprising a session emotional state measure recovery pattern as it returns towards a baseline subject emotional state, and
comparing at least one of
the session mind state recovery profile with a baseline mind state recovery profile,
the session body state recovery profile with a baseline body state recovery profile,
the session emotional state recovery profile with a baseline emotional state recovery profile, and
wherein the health state of the subject is improved if a recovery time interval of at least one of the session mind state recovery profile, the session body state recovery profile and the session emotional state recovery profile is decreased compared to the baseline mind state recovery profile, the baseline body state recovery profile and the baseline emotional state recovery profile; and wherein determining the baseline mind state recovery profile, the baseline body state recovery profile and the baseline emotional state recovery profile comprises, during a baseline session of the subject,
determining the baseline subject mind state based on neural activity signals from the subject-internal signals received during the baseline session,
determining the baseline subject body state based on muscle activity signals from the subject-internal signals received during the baseline session,
determining the baseline subject emotional state based on heart rate variability signals from the subject-internal signals received during the baseline session,
exposing the subject to a stressor presented by the user interface in communication with the processor, where the stressor includes at least one of,
an emotional stressor comprising visual image or scene and/or audio information capable of producing a stressed subject emotional state, and
a physical stressor comprising a subject body condition or stimulus capable of producing a stressed subject physical state,
terminating exposure of the subject to the stressor presented on the user interface by the processor,
receiving, by the processor, subject-internal signals during and after exposing the subject to the stressor,
determining a stressed subject mind state based on neural activity signals from the subject-internal signals received during exposure of the stressor,
determining a stressed subject body state based on muscle activity signals from the subject-internal signals received during exposure of the stressor, and
determining a stressed subject emotional state based on heart rate variability signals from the subject-internal signals received during the exposure of the stressor.

2. The method of claim 1, wherein:
the neural activity signals comprise electroencephalography (EEG) signals; and
the muscle activity signals comprise electromyography (EMG) signals.

3. The method of claim 1, further comprising determining:
a mind state recovery time interval across which the stressed subject mind state exhibits as it returns to within a first target percentage of the baseline subject mind state;
a body state recovery time interval across which the stressed subject body state exhibits as it returns to within a second target percentage of the baseline subject body state; and
an emotional state recovery time interval across which the stressed subject emotional state exhibits as it returns to within a third target percentage of the baseline subject emotional state.

4. The method of claim 3, wherein:
the subject's impaired function comprises a physically impaired body part; and
determining the health state of the subject further comprises determining whether the mind state recovery time interval, the body state recovery time interval, and the emotional state recovery time interval decrease over time following multiple subject physical skill development sessions,
wherein each subject physical skill development session comprises presenting functional skill development activities to the subject simultaneous with presenting current mind state biofeedback and current body state feedback to the subject, and
wherein presenting the functional skill development activities comprises presenting visual information showing usage of an unimpaired body part corresponding to the physically impaired body part in a mirror image manner during subject viewing of the visual information.

5. The method of claim 4, further comprising:
receiving, by the processor, levels of subject-external signals, the subject-external signals are generated external to the subject's body and include an ambient temperature level, an ambient relative humidity level, and an ambient noise level;
determining subject performance and subject outcome measures corresponding to each physical skill development session;
correlating the levels of subject-external signals with the subject performance and subject outcome measures; and
determining whether the subject performance and subject outcome measures across different physical skill development sessions were adversely affected by the level of one or more subject-external signals exceeding a target or threshold level or falling outside of a target or threshold range.

6. The method of claim 5, wherein the levels of subject-external signals further comprise at least one of an ambient light level, an ambient atmospheric pressure, altitude level, an ambient magnetic field intensity level, and an ambient electromagnetic signal level within at least one electromagnetic signal frequency band.

7. The method of claim 5, further comprising automatically transferring by way of a cellular network communication at least one of the determined subject performance measures and the subject outcome measures to a set of servers, without subject initiation, management, and acknowledgment.

8. The method of claim 7 further comprises
providing the sensor device which includes a set of wearable subject-internal signal sensing devices configured for sensing the subject-internal signals, the set of wearable subject-internal signal sensing devices includes:
a head mountable sensing apparatus configured for sensing subject electroencephalography (EEG) signals; and
at least one of
a forearm mountable sensing apparatus configured for sensing subject electromyography (EMG) signals generated by particular subject forearm and hand muscles,
a neck mountable sensing apparatus configured for sensing subject EMG signals generated by particular subject neck muscles,
a chest mountable sensing apparatus configured for sensing subject EMG signals generated by particular subject upper torso muscles,
a waist mountable apparatus configured for sensing subject EMG signals generated by particular subject abdominal, waist, hip, and gluteal region muscles,
an upper leg mountable sensing apparatus configured for sensing subject EMG signals generated by subject upper leg muscles, and
a lower leg mountable apparatus configured for sensing subject EMG signals generated by particular subject lower leg muscles; and
providing a set of subject-external signal sensing devices configured for sensing the subject-external signals, wherein the set of subject-external sensing devices includes
a set of accelerometers and/or gyroscopes carried by the set of subject-internal signal sensing devices,
an ambient temperature sensor,
an ambient humidity sensor,
an ambient noise sensor, and
at least one of an ambient lighting level sensor, an ambient atmospheric pressure or elevation level sensor, and an ambient magnetic field intensity sensor.

9. The method of claim 5, wherein the determining subject outcome measures comprises:
receiving current subject outcome data representing a current subject outcome resulting from subject performance or attempted performance of a functional skill development activity sequence;
comparing the received current subject outcome data with corresponding target subject outcome data to determine an extent to which the current subject outcome matches the target subject outcome for the functional skill development activity sequence, and
wherein the current subject outcome data comprises at least one of image data, audio data, electronic drawing pad, electronic stylus data, captured keyboard input, accelerometer, gyroscope data, and pressure mat data generated by an apparatus with which the subject interacts.

10. The method of claim 5 further comprises storing subject information in a database, wherein the subject information includes:
received subject-internal signal histories, including subject mind state measures, body state measures, and emotional state measures derived therefrom,
received subject-external signal histories, and
target subject outcome data representing target outcomes of subject performance or attempted performance of particular types of functional development activity sequences.

11. The method of claim 1, further comprising:
determining an extent of subject torso or trunk rotational asymmetry; and
determining whether the extent of subject torso or trunk rotational asymmetry is greater than a target or threshold torso or trunk rotational asymmetry value, wherein the target or threshold torso or trunk rotational asymmetry value equals 9 mm+/−20%.

12. The method of claim 11, wherein determining the health state of the subject further comprises determining whether the extent of subject torso or trunk rotational asymmetry decreases over time to less than or equal to the target or threshold torso or trunk rotational asymmetry value following multiple subject physical skill development sessions.

13. The method of claim 1 further comprises providing a visual interface configured for presenting biofeedback information to the subject simultaneous with presenting functional skill development activity sequences to the subject.

14. The method of claim 1, wherein the selectively displaying the functional skill activities are automatically and adaptively displayed based on the current subject body state, the current subject mind state and the current subject emotional state measures.

15. The method of claim 1, wherein the functional skill development activities comprise mind state training sequences, body state training sequences, and emotional state training sequences.

16. A computerized method for treating a human subject with an impaired function due to neurological damage through the development of physical, mental and emotional skills, the method comprising:
fitting the subject with a sensor device having sensors for sensing subject-internal signals during a treatment session;
receiving, by a processor, the sensed subject-internal signals, wherein the processor is configured to communicate with the sensor device to receive the sensed subject-internal signals;
continuously calculating on a real-time basis during the treatment session by the processor,
a current subject mind state measure based on neural activity signals of the received subject-internal signals, a
current subject body state measure based on muscle activity signals of the received subject-internal signals, and
a current subject emotional state measure based on heart rate variability signals of the received subject-internal signals;
administering by the processor during the treatment session a set of functional development activity sequence or training exercises for the subject to perform depending on the continuously calculated current subject mind state measure, current subject body state measure and current subject emotional state measure, wherein administering comprises
displaying on the user interface the set of functional development activity sequence targeted to rehabilitate the impaired function of the subject when
the continuously calculated current subject body state measure is at the target body state measure,
the continuously calculated current subject mind state measure is at the target mind state, and
the continuously calculated current subject emotional state is at the target emotional state,
displaying on the user interface mind state training exercises when the continuously calculated current subject mind state is not at the target mind state to direct the continuously calculated current subject mind state to the target mind state,
displaying on the user interface body state training exercises when the continuously calculated current subject body state is not at the target body state to direct the continuously calculated current subject body state measure to the target body state,
displaying on the user interface emotional state training exercises when the continuously calculated current subject emotional state is not at the target emotional state to direct the continuously calculated current subject emotional state to the target emotional state, and
wherein performing the set of functional development activity sequence when the continuously calculated current subject mind state, continuously calculated current subject body state and continuously calculated current subject emotional state are at the target mind state, target body state and target emotional state optimizes the subject's performance to improve recovery of the impaired function; determining a health state of the subject comprising
determining at least one of,
a session mind state recovery profile comprising a session mind state measure recovery pattern as it returns towards a baseline subject mind state,
a session body state recovery profile comprising a session mind state measure recovery pattern as it returns towards a baseline subject body state,
a session emotional state recovery profile comprising a session emotional state measure recovery pattern as it returns towards a baseline subject emotional state, and
comparing at least one of
the session mind state recovery profile with a baseline mind state recovery profile,
the session body state recovery profile with a baseline body state recovery profile,
the session emotional state recovery profile with a baseline emotional state recovery profile, and
wherein the health state of the subject is improved if a recovery time interval of at least one of the session mind state recovery profile, the session body state recovery profile and the session emotional state recovery profile is decreased compared to the baseline mind state recovery profile, the baseline body state recovery profile and the baseline emotional state recovery profile.

17. The method of claim 16 wherein determining the baseline mind state recovery profile, the baseline body state recovery profile and the emotional state recovery profile comprises, during a baseline session of the subject,
determining the baseline subject mind state based on neural activity signals from the subject-internal signals received during the baseline session,
determining the baseline subject body state based on muscle activity signals from the subject-internal signals received during the baseline session,
determining the baseline subject emotional state based on heart rate variability signals from the subject-internal signals received during the baseline session,
exposing the subject to a stressor presented by the user interface in communication with the processor, where the stressor includes at least one of,
an emotional stressor comprising visual image or scene and/or audio information capable of producing a stressed subject emotional state, and
a physical stressor comprising a subject body condition or stimulus capable of producing a stressed subject physical state,
terminating exposure of the subject to the stressor presented on the user interface by the processor,
receiving, by the processor, subject-internal signals during and after exposing the subject to the stressor,
determining a stressed subject mind state based on neural activity signals from the subject-internal signals received during exposure of the stressor,
determining a stressed subject body state based on muscle activity signals from the subject-internal signals received during exposure of the stressor, and determining a stressed subject emotional state based on heart rate variability signals from the subject-internal signals received during the exposure of the stressor.

18. The method of claim 17 further comprises determining:
a mind state recovery time interval across which the stressed subject mind state returns to within a first target percentage of the baseline subject mind state;
a body state recovery time interval across which the stressed subject body state returns to within a second target percentage of the baseline subject body state; and
an emotional state recovery time interval across which the stressed subject emotional state returns to within a third target percentage of the baseline subject emotional state.

19. The method of claim 16, further comprising:
receiving, by the processor, levels of subject-external signals, the subject-external signals are generated external to the subject's body and include an ambient temperature level, an ambient relative humidity level, and an ambient noise level;
determining subject performance and subject outcome measures corresponding to each physical skill development session;
correlating the levels of subject-external signals with the subject performance and subject outcome measures; and
determining whether the subject performance and subject outcome measures across different physical skill development sessions were adversely affected by the level of one or more subject-external signals exceeding a target or threshold level or falling outside of a target or threshold range.

20. The method of claim 19 further comprises
providing the sensor device which includes a set of wearable subject-internal signal sensing devices configured for sensing the subject-internal signals, the set of wearable subject-internal signal sensing devices includes:
a head mountable sensing apparatus configured for sensing subject electroencephalography (EEG) signals;
at least one of
a forearm mountable sensing apparatus configured for sensing subject electromyography (EMG) signals generated by particular subject forearm and hand muscles,
a neck mountable sensing apparatus configured for sensing subject EMG signals generated by particular subject neck muscles,
a chest mountable sensing apparatus configured for sensing subject EMG signals generated by particular subject upper torso muscles,
a waist mountable apparatus configured for sensing subject EMG signals generated by particular subject abdominal, waist, hip, and gluteal region muscles,
an upper leg mountable sensing apparatus configured for sensing subject EMG signals generated by subject upper leg muscles, and
a lower leg mountable apparatus configured for sensing subject EMG signals generated by particular subject lower leg muscles; and
providing a set of subject-external signal sensing devices configured for sensing the subject-external signals, wherein the set of subject-external sensing devices includes
a set of accelerometers and/or gyroscopes carried by the set of subject-internal signal sensing devices,
an ambient temperature sensor,
an ambient humidity sensor,
an ambient noise sensor, and
at least one of an ambient lighting level sensor, an ambient atmospheric pressure or elevation level sensor, and an ambient magnetic field intensity sensor.

21. The method of claim 16, further comprising:
determining an extent of subject torso or trunk rotational asymmetry; and
determining whether the extent of subject torso or trunk rotational asymmetry is greater than a target or threshold torso or trunk rotational asymmetry value, wherein the target or threshold torso or trunk rotational asymmetry value equals 9 mm+/−20%.

\* \* \* \* \*